United States Patent
Pozvonkov et al.

(10) Patent No.: US 9,905,871 B2
(45) Date of Patent: Feb. 27, 2018

(54) LOW TEMPERATURE SOLID OXIDE CELLS

(71) Applicant: FCET, LLC, Roswell, GA (US)

(72) Inventors: Mikhail Pozvonkov, Cumming, GA (US); Mark A. Deininger, Roswell, GA (US)

(73) Assignee: FCET, INC., Roswell, GA (US)

( * ) Notice: Subject to any disclaimer, the term of this patent is extended or adjusted under 35 U.S.C. 154(b) by 0 days.

(21) Appl. No.: 14/904,570

(22) PCT Filed: Jul. 14, 2014

(86) PCT No.: PCT/US2014/046519
§ 371 (c)(1),
(2) Date: Jan. 12, 2016

(87) PCT Pub. No.: WO2015/009618
PCT Pub. Date: Jan. 22, 2015

(65) Prior Publication Data
US 2016/0149249 A1    May 26, 2016

Related U.S. Application Data

(60) Provisional application No. 61/857,856, filed on Jul. 24, 2013, provisional application No. 61/846,411, filed on Jul. 15, 2013.

(51) Int. Cl.
*H01M 8/1007* (2016.01)
*H01M 8/1016* (2016.01)
(Continued)

(52) U.S. Cl.
CPC ............. *H01M 8/1007* (2016.02); *C25B 1/46* (2013.01); *C25B 9/08* (2013.01); *C25B 15/02* (2013.01);
(Continued)

(58) Field of Classification Search
CPC .... H01M 8/1009; H01M 4/9016; H01M 4/92; H01M 8/04186; H01M 8/1097;
(Continued)

(56) References Cited

U.S. PATENT DOCUMENTS 2,048,912 A    7/1936    Ziska et al.
2,141,477 A    12/1938    Loesch
(Continued)

FOREIGN PATENT DOCUMENTS

CA    2789281 C    11/2015
DE    295148 A5    10/1991
(Continued)

OTHER PUBLICATIONS

English-language abstract for SU 923232 A1 Filippov et al.
(Continued)

*Primary Examiner* — Oi K Conley
(74) *Attorney, Agent, or Firm* — Thrive IP®; Jeremy M. Stipkala

(57) ABSTRACT

The present invention provides solid oxide cells such as fuel cells, electrolyzers, and sensors comprising an electrolyte having an interface between an yttria-stabilized zirconia material and a glass material, in some embodiments. Other embodiments add an interface between a platinum oxide material and the yttria-stabilized zirconia material in the electrolyte. Further embodiments of solid oxide cells have an ion-conducting species such as an ionic liquid or inorganic salt in contact with at least one electrode of the cell. Certain embodiments provide room temperature operation of solid oxide cells.

15 Claims, 9 Drawing Sheets

(51) Int. Cl.
   *H01M 8/1097* (2016.01)
   *H01M 8/1213* (2016.01)
   *H01M 8/1253* (2016.01)
   *H01M 8/1286* (2016.01)
   *H01M 4/90* (2006.01)
   *H01M 4/92* (2006.01)
   *H01M 8/04186* (2016.01)
   *C25B 15/02* (2006.01)
   *C25B 15/08* (2006.01)
   *C25B 1/46* (2006.01)
   *C25B 9/08* (2006.01)
   *H01M 8/1009* (2016.01)
   *H01M 8/241* (2016.01)
   *H01M 8/2425* (2016.01)
   *H01M 8/2455* (2016.01)
   *H01M 8/124* (2016.01)
   *G01N 27/407* (2006.01)

(52) U.S. Cl.
   CPC ........... *C25B 15/08* (2013.01); *H01M 4/9016* (2013.01); *H01M 4/92* (2013.01); *H01M 8/04186* (2013.01); *H01M 8/1016* (2013.01); *H01M 8/1097* (2013.01); *H01M 8/1213* (2013.01); *H01M 8/1253* (2013.01); *H01M 8/1286* (2013.01); *G01N 27/4073* (2013.01); *H01M 4/905* (2013.01); *H01M 4/9025* (2013.01); *H01M 8/1009* (2013.01); *H01M 8/241* (2013.01); *H01M 8/2425* (2013.01); *H01M 8/2455* (2013.01); *H01M 2008/1293* (2013.01); *H01M 2300/0002* (2013.01); *H01M 2300/002* (2013.01); *H01M 2300/0071* (2013.01); *H01M 2300/0077* (2013.01); *H01M 2300/0094* (2013.01); *Y02E 60/525* (2013.01); *Y02P 70/56* (2015.11)

(58) Field of Classification Search
   CPC ............. H01M 8/1213; H01M 8/1253; H01M 8/1286; C25B 1/46; C25B 9/08; C25B 15/08
   See application file for complete search history.

(56) References Cited

U.S. PATENT DOCUMENTS

| | | |
|---|---|---|
| 2,334,294 A | 11/1943 | Stevens |
| 2,470,796 A | 5/1949 | Stromquist |
| 2,530,110 A | 11/1950 | Woodyard |
| 2,792,807 A | 5/1957 | Cummings |
| 3,404,039 A | 10/1968 | Mitoff |
| 3,503,809 A | 3/1970 | Spacil |
| 3,673,452 A | 6/1972 | Brennen |
| 3,679,712 A | 7/1972 | Firestone |
| 3,773,555 A | 11/1973 | Cotton et al. |
| 3,947,292 A | 3/1976 | Jackovitz et al. |
| 3,962,490 A | 6/1976 | Ward |
| 3,967,149 A | 6/1976 | Eaton et al. |
| 3,984,717 A | 10/1976 | Romanowski et al. |
| 4,142,024 A | 2/1979 | Van den Berghe et al. |
| 4,267,483 A | 5/1981 | Nakajima et al. |
| 4,279,974 A * | 7/1981 | Nishio ................. C25C 7/04 429/104 |
| 4,297,150 A | 10/1981 | Foster et al. |
| 4,307,061 A | 12/1981 | Sarholz |
| 4,318,894 A | 3/1982 | Hensel et al. |
| 4,358,892 A | 11/1982 | Turillon et al. |
| 4,530,340 A | 7/1985 | Totman |
| 4,686,201 A | 8/1987 | Porter et al. |
| 4,687,567 A | 8/1987 | Porter et al. |
| 4,743,793 A | 5/1988 | Toya et al. |
| 4,772,577 A | 9/1988 | Rittler |
| 4,786,267 A | 11/1988 | Toya et al. |
| 4,826,462 A | 5/1989 | Lenk |
| 4,828,934 A | 5/1989 | Pinkhasov |
| 4,853,582 A | 8/1989 | Sato et al. |
| 4,881,913 A | 11/1989 | Mann |
| 4,925,886 A | 5/1990 | Atkins et al. |
| 4,935,265 A | 6/1990 | Pike |
| 4,937,484 A | 6/1990 | Ishino |
| 4,961,917 A | 10/1990 | Byrne |
| 4,963,112 A | 10/1990 | Benedikt et al. |
| 4,963,390 A | 10/1990 | Lipeles et al. |
| 4,972,811 A | 11/1990 | Baresel et al. |
| 5,015,358 A | 5/1991 | Reed et al. |
| 5,021,398 A | 6/1991 | Sharma et al. |
| 5,028,467 A | 7/1991 | Maruyama et al. |
| 5,064,791 A | 11/1991 | Ohtsuka et al. |
| 5,073,410 A | 12/1991 | Paz-Pujalt |
| 5,100,632 A | 3/1992 | Dettling et al. |
| 5,106,706 A | 4/1992 | Singh et al. |
| 5,109,178 A | 4/1992 | Yoshida et al. |
| 5,130,210 A | 7/1992 | Iwasaki et al. |
| 5,274,298 A | 12/1993 | Cassidy et al. |
| 5,279,111 A | 1/1994 | Bell et al. |
| 5,312,585 A | 5/1994 | Jones |
| 5,342,703 A | 8/1994 | Kawasaki et al. |
| 5,413,642 A | 5/1995 | Alger |
| 5,423,285 A | 6/1995 | Paz de Araujo et al. |
| 5,468,679 A | 11/1995 | Paz de Araujo et al. |
| 5,472,795 A | 12/1995 | Aita |
| 5,494,700 A | 2/1996 | Anderson et al. |
| 5,518,603 A | 5/1996 | Furuhashi et al. |
| 5,551,994 A | 9/1996 | Schriever |
| 5,580,497 A | 12/1996 | Balachandran et al. |
| 5,601,869 A | 2/1997 | Scott et al. |
| 5,612,082 A | 3/1997 | Azuma et al. |
| 5,645,634 A | 7/1997 | Ogi et al. |
| 5,689,797 A | 11/1997 | Chelluri et al. |
| 5,699,035 A | 12/1997 | Ito et al. |
| 5,753,385 A | 5/1998 | Jankowski et al. |
| 5,766,787 A | 6/1998 | Watanabe et al. |
| 5,805,973 A | 9/1998 | Coffinberry et al. |
| 5,817,436 A | 10/1998 | Nishijima et al. |
| 5,827,570 A | 10/1998 | Russell |
| 5,905,363 A | 5/1999 | Helbing et al. |
| 5,919,519 A | 7/1999 | Tallis |
| 5,952,769 A | 9/1999 | Budaragin |
| 5,968,463 A | 10/1999 | Shelef et al. |
| 5,976,458 A | 11/1999 | Sikka et al. |
| 5,990,416 A | 11/1999 | Windisch, Jr. et al. |
| 6,040,265 A | 3/2000 | Nunan |
| 6,051,529 A | 4/2000 | Brezny |
| 6,071,464 A | 6/2000 | Funaki et al. |
| 6,093,378 A | 7/2000 | Deeba et al. |
| 6,117,581 A | 9/2000 | Shelef |
| 6,127,202 A | 10/2000 | Kapur et al. |
| 6,139,921 A | 10/2000 | Taschner et al. |
| 6,153,160 A | 11/2000 | Voss et al. |
| 6,190,634 B1 | 2/2001 | Lieber et al. |
| 6,224,993 B1 | 5/2001 | Hartvigsen et al. |
| 6,268,014 B1 | 7/2001 | Eberspacher et al. |
| 6,294,261 B1 | 9/2001 | Sangeeta et al. |
| 6,320,375 B1 | 11/2001 | Cotton et al. |
| 6,328,779 B1 | 12/2001 | He et al. |
| 6,379,712 B1 | 4/2002 | Yan et al. |
| 6,416,818 B1 | 7/2002 | Aikens et al. |
| 6,426,315 B1 | 7/2002 | Bergstrom et al. |
| 6,448,190 B1 | 9/2002 | Hayashi et al. |
| 6,476,312 B1 | 11/2002 | Bamham |
| 6,500,733 B1 | 12/2002 | Stanberry |
| 6,559,372 B2 | 5/2003 | Stanberry |
| 6,593,213 B2 | 7/2003 | Stanberry |
| 6,620,456 B2 | 9/2003 | Blanton et al. |
| 6,624,213 B2 | 9/2003 | George et al. |
| 6,663,983 B1 | 12/2003 | Darolia et al. |
| 6,683,025 B2 | 1/2004 | Amendola et al. |
| 6,686,489 B2 | 2/2004 | Celinska et al. |
| 6,736,986 B2 | 5/2004 | Stanberry |
| 6,769,152 B1 | 8/2004 | Crenshaw et al. |
| 6,773,513 B2 | 8/2004 | Ludtka |

(56) References Cited

U.S. PATENT DOCUMENTS

| | | |
|---|---|---|
| 6,824,883 B1 | 11/2004 | Benum et al. |
| 6,899,966 B2 | 5/2005 | Benum et al. |
| 6,921,557 B2 | 7/2005 | Jacobson et al. |
| 6,969,484 B2 | 11/2005 | Horiguchi et al. |
| 6,991,867 B1 * | 1/2006 | Zhu .................... B01D 53/326 429/218.1 |
| 6,998,187 B2 | 2/2006 | Finnerty et al. |
| 7,045,238 B2 | 5/2006 | Gottman et al. |
| 7,083,710 B2 | 8/2006 | Scheer et al. |
| 7,117,099 B2 | 10/2006 | Stassner et al. |
| 7,156,979 B2 | 1/2007 | Benum et al. |
| 7,161,124 B2 | 1/2007 | Kisner et al. |
| 7,163,759 B2 | 1/2007 | Milliken et al. |
| 7,211,292 B1 | 5/2007 | Budaragin |
| 7,227,736 B2 | 6/2007 | Shioga et al. |
| 7,229,597 B2 | 6/2007 | Patchett et al. |
| 7,235,171 B2 | 6/2007 | Taniguchi |
| 7,250,147 B2 | 7/2007 | Tour et al. |
| 7,255,956 B2 | 8/2007 | McElroy et al. |
| 7,271,333 B2 | 9/2007 | Fabick et al. |
| 7,279,047 B2 | 10/2007 | Melnik et al. |
| 7,300,684 B2 | 11/2007 | Boardman et al. |
| 7,306,823 B2 | 12/2007 | Sagar et al. |
| 7,318,763 B2 | 1/2008 | Tsakalakos et al. |
| 7,351,488 B2 | 4/2008 | Visco et al. |
| 7,399,720 B1 | 7/2008 | Brow et al. |
| 7,488,392 B2 | 2/2009 | Benum et al. |
| 7,491,376 B2 | 2/2009 | Barron et al. |
| 7,645,543 B2 * | 1/2010 | Visco .................... H01M 6/04 429/137 |
| 7,718,221 B2 | 5/2010 | Budaragin et al. |
| 8,623,301 B1 | 1/2014 | Deininger et al. |
| 9,353,434 B2 | 5/2016 | Deininger et al. |
| 9,670,586 B1 | 6/2017 | Deininger et al. |
| 2001/0003010 A1 | 6/2001 | Pham et al. |
| 2001/0041278 A1 | 11/2001 | Hashimoto et al. |
| 2002/0004028 A1 | 1/2002 | Margrave et al. |
| 2002/0006470 A1 | 1/2002 | Eberspacher et al. |
| 2002/0041928 A1 | 4/2002 | Budaragin |
| 2002/0182468 A1 | 12/2002 | Janousek et al. |
| 2002/0187091 A1 | 12/2002 | Deevi |
| 2004/0013924 A1 | 1/2004 | Park et al. |
| 2004/0023101 A1 | 2/2004 | Jacobson et al. |
| 2004/0033319 A1 | 2/2004 | Yamada et al. |
| 2004/0061114 A1 | 4/2004 | Yan et al. |
| 2004/0076867 A1 | 4/2004 | Day et al. |
| 2004/0188323 A1 | 9/2004 | Tzatzov et al. |
| 2005/0089684 A1 | 4/2005 | Barron et al. |
| 2005/0201919 A1 | 9/2005 | Yu et al. |
| 2005/0247339 A1 | 11/2005 | Bamham et al. |
| 2005/0257857 A1 | 11/2005 | Benum et al. |
| 2005/0277024 A1 | 12/2005 | West et al. |
| 2006/0024547 A1 | 2/2006 | Waldbillig et al. |
| 2006/0035130 A1 | 2/2006 | Noda et al. |
| 2006/0040168 A1 | 2/2006 | Sridhar |
| 2006/0063052 A1 | 3/2006 | Hu et al. |
| 2006/0194117 A1 | 8/2006 | Paulsen |
| 2006/0196419 A1 | 9/2006 | Tudhope et al. |
| 2006/0198965 A1 | 9/2006 | Tudhope et al. |
| 2006/0199057 A1 | 9/2006 | Hiwatashi |
| 2006/0231549 A1 | 10/2006 | Kisner et al. |
| 2006/0234855 A1 | 10/2006 | Gorte et al. |
| 2007/0015002 A1 | 1/2007 | Narula et al. |
| 2007/0059576 A1 | 3/2007 | Jacobson et al. |
| 2007/0077440 A1 | 4/2007 | Gawalt |
| 2007/0116966 A1 | 5/2007 | Mellott et al. |
| 2007/0184322 A1 | 8/2007 | Huang et al. |
| 2007/0227120 A1 | 10/2007 | Yodice et al. |
| 2007/0237998 A1 | 10/2007 | Armstrong et al. |
| 2007/0262059 A1 | 11/2007 | Boardman et al. |
| 2007/0273070 A1 | 11/2007 | Badding et al. |
| 2008/0029494 A1 | 2/2008 | Tudhope et al. |
| 2008/0063587 A1 | 3/2008 | Strano et al. |
| 2008/0118777 A1 | 5/2008 | Li et al. |
| 2008/0131749 A1 | 6/2008 | Hilliard |
| 2008/0299436 A1 | 12/2008 | Striker et al. |
| 2008/0318092 A1 | 12/2008 | Sridhar et al. |
| 2009/0087697 A1 | 4/2009 | Ramanathan et al. |
| 2009/0098289 A1 | 4/2009 | Deininger et al. |
| 2009/0218311 A1 | 9/2009 | Jiang et al. |
| 2010/0066036 A1 | 3/2010 | Cruse et al. |
| 2010/0275979 A1 | 11/2010 | Maruyama |
| 2012/0171596 A1 | 7/2012 | Hillard |
| 2013/0146469 A1 | 6/2013 | Budaragin et al. |
| 2014/0319317 A1 | 10/2014 | Lai et al. |
| 2016/0168734 A1 | 6/2016 | Budaragin et al. |
| 2017/0146481 A1 | 5/2017 | Pozvonkov et al. |
| 2017/0162896 A1 | 6/2017 | Pozvonkov et al. |

FOREIGN PATENT DOCUMENTS

| | | |
|---|---|---|
| EP | 0414575 A1 | 2/1991 |
| EP | 0513982 A2 | 11/1992 |
| EP | 97/0682696 B1 | 12/1997 |
| EP | 01/1088908 A2 | 4/2001 |
| EP | 1693914 A1 | 8/2006 |
| EP | 1103080 B1 | 8/2008 |
| FR | 2617507 | 1/1989 |
| GB | 1049428 | 11/1966 |
| GB | 2460877 A | 12/2009 |
| JP | 2010-277771 A | 12/2010 |
| KR | 10-2010-0073833 A | 7/2010 |
| SU | 923232 A1 | 7/1980 |
| WO | 85/00997 | 3/1985 |
| WO | 92/010651 | 6/1992 |
| WO | 94/018299 | 8/1994 |
| WO | 97/025146 | 7/1997 |
| WO | 02/014657 A1 | 2/2002 |
| WO | 03/021004 | 3/2003 |
| WO | 03/070640 | 8/2003 |
| WO | 2004/104261 A1 | 12/2004 |
| WO | 2005/019324 | 3/2005 |
| WO | 2005/035951 A1 | 4/2005 |
| WO | 2007/009104 | 1/2007 |
| WO | 2008/123484 | 10/2008 |
| WO | 2008/130433 | 10/2008 |
| WO | 2009/126875 A2 | 10/2009 |
| WO | 2009/129380 A2 | 10/2009 |
| WO | 2011/100361 A2 | 8/2011 |
| WO | 2015009618 | 1/2015 |

OTHER PUBLICATIONS

Written Opinion for PCT/US2011/024242 dated Oct. 28, 2011.
Canadian Office Action in Canadian Patent Application No. 2,789,281, dated Nov. 15, 2013 (4 pages).
Canadian Office Action in Canadian Patent Application No. 2,789,281, dated Jul. 28, 2014 (3 pages).
Supplementary Partial European Search Report for European Application No. EP 11 74 2752, National Phase of PCT/US2011/024242, dated Mar. 3, 2015 (6 pages).
Notes, "ASM Fuel Cell Overview," (Oct. 2003) by Paul Fisher (2 pages).
Notes, "Fuel Cells 2004," (May 2004) by Paul Fisher (7 pages).
Notes, "CAMP/Nano-Network," (Jun. 2004) by Paul Fisher (2 pages).
Notes, "ASM/Columbus, OH," (Oct. 2004) by Paul Fisher (3 pages).
Notes, "Feb. 7, 2007," (Feb. 2007) by Paul Fisher (25 pages).
Notes, "Notes on Advances in SOFCs II," (Dec. 2007) by Paul Fisher (9 pages) (referencing "Advances in Solid Oxide Fuel Cells II," (N.P. Bansal et al., Eds., John Wiley & Sons 2007)).
Sandrine Colson-Inam, "Solid Oxide Fuel Cells Ready to Market?" FuelCellToday.com (Jan. 2004).
Sylvia Baron, "Intermediate Temperature (500-850) SOFC's Explained," FuelCellToday.com (Jan. 2004).
Gregor Knoner et al., "Enhanced oxygen diffusivity in interfaces of nanoctystalline $ZrO_2.Y_2O_3$," PNAS vol. 100 No. 7, 3870-73 (Apr. 2003).
Matthew Seabaugh, Ph.D. et al., "Tailor Made," Ceramic Industry 24-27 (Apr. 2007).

(56) References Cited

OTHER PUBLICATIONS

"Development of a Portable Solid Oxide Fuel Cell," NanoDynamics, Inc. Presentation (May 2004).
William Smith, "Regenerative Fuel Cells for Renewable Energy Storage," Presentation (May 2004).
Zhenguo G. Yang et al., "Solid Oxide Fuel Cells, Materials for the Bipolar Plates of SOFC," Advanced Materials & Processes, 34-37 (Jun. 2003).
N. P. Brandon et al., "Development of Metal supported Solid Oxide Fuel Cells for Operation at 500-600 degrees celsius," Journal of Materials vol. 13, 253-56 (Jun. 2004).
Dillon D. Fong et al., "Ferroelectricity in Ultrathin Perovskite Films," Science vol. 304, 1650-53 (Jun. 2004).
"Revolution, Mobile, Powerful," Electrical Contractor 5-7 (Jun. 2004).
Zongping Shao et al., "A thermally self-sustained micro solid-oxide fuel-cell stack with high power density," Nature, 795-98 (Jun. 2005).
Emmeline Chen, "Solid-Oxide Fuel Cells Stack Up to Efficient Clean Power," Research Highlights, S&TR, 17-19 (Sep. 2002).
Material Solutions Conference Final Program, pp. 37, 65-67 (Oct. 2003).
Steven G. Chalk and S. R. Venkateswaran, "Is there a Continuing Role for the Federal Government in Fuel Cell R&D for Transportation?" 1998 Fuel Cell Seminar (Nov. 1998).
W.N. Lawless, "Honeycomb Fuel Cell," CeramPhysics. Inc. (Nov. 2003).
"World's Highest Efficiency for 1kW Class Power Generation," Kyocera (Dec. 2003) (accessed at http://global.kyocera.com/news/2003/1205.html on Aug. 2, 2006).
K. Muthukkumaran et al., "Ionic Conductivity Measurements in Gadolinia Doped Ceria," Int. Symp. Res. Students Mater. Sci. Eng. (Dec. 2004).
K. Huang, "Oxide-ion conducting ceramics for solid oxide fuel cells," Journal of Material Science, vol. 36, 1093-1098 (2001).
V. V. Kharton et al., "Ceria-Based Materials for Solid Fuel Cells," Journal of Materials Science, vol. 36, 1105-1117, (2001).
"Fuel Cells for Building and Vehicles," ORNL Review vol. 35 No. 2 (2002).
Austin Weber, "Fuel Cells Fact Not Fiction," Assembly 70-77 (2003).
"Cool fuel cells could revolutionize Earth's energy resources," Nanodynamics, Inc. (2004).
"Can gold be employed as a fuel cell catalyst," Catgold Issue No. 8, 3 (2005).
Michael Hill, "Material Trends in SOFC Systems," Ceramic Industry/Ceramic Energy 6-8 (2005).
Igor Kosacki, "Nanoscaled Oxide Thin Films for Energy Conversion," NATO Science Series II, 1-18 (2005).
E. Koep el al., "Microstructure & Electrochemical Properties" J. Power Sources 161, 250-255 (2006).
D. Todorovsky et al., "Spray-Pyrolysis, Deep and Spin-Coating Deposition of Thin Films and Their Characterization," Journal of the University of Chemical Technology and Metallurgy, vol. 41, No. 1, 93-96 (2006).
Binod Kumar et al., "Electrical Properties of Heterogeneously Doped Yttria Stabilized Zirconia" (undated).
C. Bentley et al., "Direct Fuel Cell Commercialization," Fuel Cell Energy, Inc. (undated).
Eric Wachsman, "Fundamentals of Ionic Transport," High Temperature Electrochemistry Center (accessed at http://hitech.mse.ufl.edu/Wachsman%201.htm on Jun. 23, 2006).
Henry Petroski, "Fuel Cells," American Scientist, vol. 91, 398-402 (2003).
Igor Kosacki et al., "Surface Interface-Related Conductivity in Nanometer Thick YSZ Films," Electrochemical and Solid-State Letters, 7, (12) A459-A461 (2004).
John Halloran et al., "Redefining Ceramic Fuel Cells," Ceramic Industry 25-28 (Apr. 2008).
E. Lara-Curzio "Mechanical Properties of tape cast nickel-based anode materials for solid oxide fuel cells before and after reduction in hydrogen," Acta. Mater. vol. 52 5747-5756 (2004).
"PAD: Polymer-Assisted Deposition of Metal-Oxide Films," Los Alamos National Laboratory (2006).
Maria Mercedes Gonzalez-Cuenca, Dissertation "Novel Anode Materials for Solid Oxide Fuel Cells" (2002).
Katsuyo Thornton et al.,"Nanotechnology for Fuel Cells and Batteries," NSF Workshop; Section 4 (accessed at www.cs.duke.edu . . . on Mar. 1, 2007).
"Solid Oxide Fuel Cell Compositions," Praxair (accessed at www.praxair.com on Sep. 14, 2006).
"New Metal-Oxide Process," Semiconductor International (2005) (accessed at www.reed-electronics.com on Jun. 29, 2007).
S. Kang et al., "Thin-Film Solid Oxide Fuel Cells on Porous Nickel Substrates with Multistage Nanohole Array," Journal of the Electrochemical Society, 153 (3) A554-A559 (2006).
Sol Gel Technology, (accessed at www.chemat.com/html/solgel.html on Nov. 7, 2003).
Tatsumi Ishihara et al., "Electrolytes," in High Temperature Solid Oxide Fuel Cells, Fundamentals, Design and Applications, Chapter 4, Elsevier (2003).
"Solid Oxide Fuel Cell," Wikipedia.org (accessed Oct. 3, 2007).
Evans et al., "Review on micro-fabricated micro-solid oxide fuel cell membranes," Journal of Power Sources, 194, (2009) 119-129.
Final Office Action in U.S. Appl. No. 14/104,994 dated Sep. 8, 2016 (20 pages).
Unpublished U.S. Appl. No. 14/093,445, filed Nov. 20, 2013 (77 pages).
Office Action in U.S. Appl. No. 14/093,445, dated Jan. 13, 2016 (16 pages).
Final Office Action in U.S. Appl. No. 14/093,445 dated Jun. 9, 2016 (26 pages).
Office Action in U.S. Appl. No. 12/420,457 dated Mar. 1, 2012 (5 pages).
Final Office Action in U.S. Appl. No. 12/420,457 dated May 22, 2013 (11 pages).
Office Action in U.S. Appl. No. 12/420,457 dated Sep. 24, 2013 (9 pages).
Final Office Action in U.S. Appl. No. 10/440,802 (Now U.S. Appl. No. 7,718,221) dated Oct. 23, 2008 (12 pages).
Office Action in U.S. Appl. No. 13/578,195 dated Nov. 7, 2013 (12 pages).
Final Office Action in U.S. Appl. No. 13/578,195 dated Jul. 9, 2014 (11 pages).
Unpublished U.S. Appl. No. 14/104,994, filed Dec. 12, 2013 (114 pages).
Office Action in U.S. Appl. No. 14/104,994 dated May 13, 2016 (16 pages).
Unpublished U.S. Appl. No. 15/149,866, filed May 9, 2016 (114 pages).
Unpublished U.S. Appl. No. 15/151,592, filed May 11, 2016 (62 pages).
International Search Report and Written Opinion for PCT/US2014/046519 (this application), dated Oct. 28, 2014 (11 pages).
Ghosh et al., "Glass-Ceramic Sealants for Planar IT-SOFC: a Bilayered Approach for Joining Electrolyte and Metallic Interconnect," J. Electrochem. Soc., vol. 155, No. 5, pp. B473-B478 (2008).
Tsai et al., "Low-Temperature Solid Oxide Fuel Cells Utilizing Thin Bilayer Electrolytes," J. Electrochem. Soc., vol. 144, No. 5, pp. L130-L132 (1997).
Machine Translation of Detailed Description JP 5238610 B (12 pages).
Machine Translation of KR 10-2010-0073833 (8 pages).
Office Action in U.S. Appl. No. 14/981,097 dated Nov. 21, 2016 (8 pages).
Communication from European Patent Office in EP Patent Application No. 11 742 752.6 dated Nov. 8, 2016 (4 pages).
Office Action in U.S. Appl. No. 15/149,866 dated Dec. 29, 2016 (9 pages).
Fleig et al., Solid State Ionics, 2004, 174, pp. 261-270.
Office Action in U.S. Appl. No. 14/104,994 dated Apr. 17, 2017 (17 pages).

(56) References Cited

OTHER PUBLICATIONS

Communication from European Patent Office in EP Patent Application No. 11 742 752.6 dated Jun. 7, 2017 (5 pages).
Final Office Action in U.S. Appl. No. 15/149,866 dated Jul. 18, 2017 (9 pages).
Communication from European Patent Office in EP 14 826 675.2 dated Oct. 16, 2017 (6 pages).
Final Office Action in U.S. Appl. No. 14/104,994 dated Nov. 1, 2017 (16 pages).
E. Ballee et al., "Synthesis of a Thin-Layered Ionic Conductor, CeO2-Y2O3, by Atomic Layer Deposition in View of Solid Oxide Fuel Cell Applications," Chem. Mater., vol. 21 (2009) 4614-4619.
J. Britt, Photovoltaic Manufacturing Cost and Throughput Improvements for Thin Film CIGS-Based Molecules: Final Technical Report, Apr. 2002, National Renewable Energy Laboratories.
G.S. Chai et al., "Synthesis of Ordered, Uniform, Macroporous Carbons with Mesoporous Walls Templated by Aggregates of Polystyrene Spheres and Silica Particles for Use as Catalyst Supports in Direct Methanol Fuel Cells," Adv. Mater. 2004, 16, No. 22, 2057-2061.
R. Goettler, "Overview of the Rolls-Royce SOFC Technology and SECA Program," Jul. 14, 2009.
G.C. Hood et al., "Aluminum Acetates and Propionates—Their Preparation and Composition," 72 J. Am. Chem. Soc., 2094-95 (1950).
Narayanan et al., "Synthesis of Soluble Aluminium Carboxylates Directly from Aluminium Hydroxide," J. Mater. Chem., 10 (2000) 2097-104.
M. Brown, "Taking the Heat," Frontiers (Apr. 2004) pp. 34-37.
G. Can De Goor et al., "Chromophore-Zeotype Composites: Direct Synthesis of an Array of Strictly Aligned Metal-Organic Complex Chromophores in a Crystalline Silica Matrix," Adv. Mater. 1996, 8, No. 1, 65-69.
Hernadi et al., "Synthesis of MWNT-based Composite Materials with Inorganic Coating," 51 Acta Materialia (2003) pp. 1447-1452.
Garcia-Barriocanal et al., Colossal Ionic Conductivity at Interfaces of Epitaxial ZrO2:Y2O3/SrTiO3 Heterostructures, 321 Science 676 (2008), with Supporting Online Material.
Chen et al., "Photocatalytic Degradation of Methylene Blue by CNT/TiO2 Composites Prepared from MWCNT and Titanium n-Butoxide with Benzene," 45 J. Korean Ceram. Soc. (2008) 651-57.
Zhu et al., "Preparation and Characterization of New Photocatalyst Combined MWCNTs with TiO2 Nanotubes," 17 Trans. Nonferrous Met. Soc. China (2007) s1117-s1121.
Latu-Romain et al., "Growth Parameters and Shape Specific Synthesis of Silicon Nanowires by the VLS Method," 10 J. Nanopart Res. (2008) 1287-91.
Civale et al., "Aspects of Silicon Nanowire Synthesis by Aluminum-Catalyzed Vapor-Liquid-Solid Mechanism," Proceedings of 7th Annual Workshop on Semiconductor Advances for Future Electronics (SAFE 2004), Nov. 25-26, 2004, Veldhoven, The Netherlands,Publ. STW, ISBN 90-73461-43-X, pp. 692-696.
Kanai et al., "Semiconductor Testing Probe Utilizing Silicon Whisker Grown by VLS (Vapor Liquid Solid) Method," Tokyo Cathode Laboratory (Jun. 6, 2001) (available at: http://www.swtest.org/swtw_library/2001proc/PDF/S7_01.pdf (accessed Feb. 20, 2009).
Hu et al., "TiO2 Thin Films Prepared from Aqueous Solution and Their Sterilizing Capability," 7 J. Ceram. Proc. Res., (2006) 49-52.
Kilner, J.A., "Feel the Strain," Nature Materials, vol. 7 (2008) 838-839.
"Zirconia Toughened Alumina ZTA—Properties and Applications of ZTA by Dynamic Ceramic Ltd." (available at http://www.azom.com/details.asp?ArticleID=3303)(accessed Jul. 12, 2007).
"High Emissivity Coating Technology Improves Heater Performance" (available at http://www.cisoilgas.com)(2012) (accessed May 30, 2012).
Report description and table of contents, "Curtailing Coke Formation in Ethylene Furnace Tubes" Nexant, Inc., Jun. 4, 2003 (available at http://nexant.ecnext.com/coms2/gi_0255-146/Curtailing-Coke-Formation-in-Ethylene.html (accessed Sep. 27, 2007).
Zervos et al., "Printed and Thin Film Photovoltaics and Batteries," (IDTechEx, Jun. 2008) (available at http://www.idtechex.com/research/reports/printed_and_thin_film_photovoltaics_and_batteries_000172.asp) (accessed Mar. 5, 2009).
Z.L. Wang, T.S. Ahmad and M.A. El-Sayed, "Steps, ledges and kinks on the surfaces of platinum nanoparticles of different shapes," Surface Science, 380,302 (1997).
G. Rupprechter, K. Hayek and H. Hofmeister, "Electron microscopy of thin-film model catalysts: activation of alumina-supported rhodium nanoparticles, "Journal of Catalysts, 173, 409 (1998).
Zhong Lin Wang and Xiangdong Feng, "Polyhedral shapes of CeO2 nanoparticles," J. Phys. Chem. B, 107, 13563-66 (2003).
Roberet Schlogl and Shaifah Bee Abd Hamid, "Nanocatalysts: Mature Science Revisited or Something Really New?," Angew. Chem. Int. Ed., 43, 1628 (2004).
M. Adlim, Mohamad Abu Bakar, Kong Yong Liew and Jamil Ismail, "Synthesis of chitosan-stabilized platinum and palladium nanoparticles and their hydrogenation activity," Journal of Molecular Catalysis A, 212, 141 (2004).
V.K. Kapur, A. Bansal, O. I. Asensio, P. Le and N. K. Shigeoka, "Fabrication of CIGS Solar Cells via Printing of Nanoparticle Precursor Inks," International Solar Electric Technology Inc. (ISET) (2004).
Tsai et al., "Low-Temperature Solid-Oxide Fuel Cells Utilizing Thin Bilayer Electrolytes," J. Electrochem. Soc., vol. 144, No. 5 (1997) pp. L130-L132.
Ghosh et al., "Glass-Ceramic Sealants for Planar IT-SOFC: a Bilayered Approach for Joining Electrolyte and Metallic Interconnect," J. Electrochem. Soc., vol. 155, No. 5 (2008) B473-B478.
K. An, "Mechanical Properties and Electrochemical Durability of Solid Oxide Fuel Cells," Ph.D. Dissertation, Virginia Polytechnic Institute and State University (2003).
A. Krishnan, "Solid Oxide Membrane Process for the Direct Reduction of Magnesium from Magnesium Oxide," Ph. D. Dissertation, Boston University (2006).
Fujishima et al., 70 Pure Appl. Chem. (1998) 2177-87.
S. Hofmann, "Gold catalyzed growth of silicon nanowires by plasma enhanced chemical vapor deposition," Journal of Applied Physics vol. 94, No. 9 (2003).
Rosnita Muhammad, Zulkafli Othaman, Samsudi Sakrani Yussof Wahab, "Vapor-liquid solid mechanism using gold colloids for the growth of GaAs nanowires," Physics Department, Faculty of Science, Universiti Teknologi Malaysia, 81310 UTM, Skudai, Johor (2008).
Igor Kosacki, Toshio Suzuki, Harlan U. Anderson, Philippe Colomban, "Raman scattering and lattice defects in nanocrystalline CeO2 thin films," Solid State Ionics 149 (2002) 99-105.
Xu, Zhigang et al., "Preparation and properties of YSZ electrolyte thin films via liquid fuel combustion chemical vapor deposition," NSF Center for Advanced Materials and Smart Structures, North Carolina A and T State, Ceramic Engineering and Science Proceedings, (2002), 23(3), 711-718.
Hampikian, J.M. et al., "The combustion chemical vapor deposition of high temperature materials," Materials Science and Engineering A267 (1999) pp. 7-18.
Supplementary European Search Report for European Patent Application No. EP 11 74 2752 dated Jul. 3, 2015 (10 pages).
Kettering University, "Fuel Cell Background Information," 2011(?) (available at: http://orgs.kettering.edu/altfuel/fcback.htm)(Accessed May 6, 2016)(11 pages).
Extended European Search Report in European Patent Application No. 14826675.2 dated Nov. 17, 2016 (9 pages).

* cited by examiner

LOW TEMPERATURE SOLID OXIDE CELLS

RELATED APPLICATIONS

This application represents the National Phase under 35 U.S.C. § 371 of international application No. PCT/US2014/046519, entitled, "LOW TEMPERATURE SOLID OXIDE CELLS," and filed internationally on Jul. 14, 2014, which international application claims benefit of priority of U.S. Provisional Patent Application No. 61/846,411, entitled, "LOW TEMPERATURE SOLID OXIDE CELLS," filed on Jul. 15, 2013; and U.S. Provisional Patent Application No. 61/857,856, entitled, "LOW TEMPERATURE SOLID OXIDE CELLS," filed on Jul. 24, 2013; the foregoing PCT/US2014/046519, 61/846,411, and 61/857,856 applications are incorporated herein by reference in their entireties.

FIELD OF INVENTION

This invention relates to solid oxide cells that can operate at relatively low temperature. Solid oxide cells include solid oxide fuel cells, solid oxide electrolyzer cells, solid oxide sensors, and components of any of the foregoing.

BACKGROUND OF THE INVENTION

Unexpectedly, Applicants have invented ways to improve the performance of solid oxide cells at lower temperatures with certain embodiments of the present invention. In certain other embodiments, Applicants have achieved heretofore unknown room-temperature operation of solid oxide cells. Lower temperature and room-temperature operation of solid oxide cells dramatically expand the universe of possible applications of these versatile cells. Also, the array of materials now available to construct these cells has exploded, since exotic and expensive high-temperature materials are no longer required.

Solid oxide fuel cells, otherwise known as ceramic fuel cells, present an environmentally friendly alternative to mainstream electrical energy production processes involving the combustion of fossil fuels. Solid oxide fuel cells enable the catalytic conversion of chemical energy stored in hydrogen into electrical energy without the concomitant release of greenhouse gases. The generation of electrical current by a solid oxide fuel cell using a hydrogen fuel results in the production of water as opposed to the production carbon dioxide, nitrous oxides, and/or sulfur dioxides associated with the combustion of fossil fuels.

In addition to hydrogen, solid oxide fuel cells are operable to function on a wide variety of fuel sources. Fuel sources in addition to hydrogen include hydrocarbons such as methane, natural gas, and diesel fuel. Hydrocarbon fuel sources are reformed into hydrogen for use with solid oxide fuel cells. Hydrocarbon reforming can be administered prior to entry into the fuel electrode or can be administered at the fuel electrode of a solid oxide fuel cell. The ability to function on a wide variety of fuels distinguishes solid oxide fuel cells from other fuel cells which lack the ability to operate on various fuels. Furthermore, the ability of solid oxide fuel cells to administer hydrocarbon feedstock reformation frees such fuel cells from the limitations associated with hydrogen production and distribution.

Currently, solid oxide fuel cells operate at high temperatures ranging from about 800° C. to 1000° C. As a result of high operating temperatures, solid oxide fuel cells require the use of exotic materials which can withstand such operating temperatures. The need for exotic materials greatly increases the costs of solid oxide fuel cells, making their use in certain applications cost-prohibitive. High operating temperatures exacerbate stresses caused by differences in coefficients of thermal expansion between components of a solid oxide fuel cell. If the operating temperature could be lowered, numerous advantages could be realized. First, less expensive materials and production methods could be employed. Second, the lower operating temperature would allow greater use of the technology. Third, energy needed to heat and operate the fuel cell would be lower, increasing the overall energy efficiency. Fourth, a lower operating temperature increases the service life of the cell. Significantly, the high operating temperature is required because of poor low temperature ion conductivity.

Proton exchange membrane ("PEM") fuel cells enjoy operational temperatures in the range 50-220° C. Typically relying on special polymer membranes to provide the electrolyte, PEM cells transmit protons across the electrolyte, rather than oxygen ions as in solid oxide fuel cells. However, high proton conductivity requires precise control of hydration in the electrolyte. If the electrolyte becomes too dry, proton conductivity and cell voltage drop. If the electrolyte becomes too wet, the cell becomes flooded. Electro-osmotic drag complicates hydration control: protons migrating across the electrolyte "drag" water molecules along, potentially causing dramatic differences in hydration across the electrolyte that inhibit cell operation. As a result, PEM cells are perhaps 40% less efficient than solid oxide fuel cells. Accordingly, it would be advantageous to obtain the low operating temperatures of the PEM fuel cell without the need to maintain strict control over electrolyte hydration, and to avoid the inefficiencies of those cells.

In certain circumstances, a solid oxide fuel cell can operate "in reverse" to electrolyze water into hydrogen gas and oxygen gas by inputting electrical energy. In other circumstances, a solid oxide electrolyzer cell can be designed primarily for use as a hydrolyzer, generating hydrogen and oxygen for later use. In still other circumstances, an electrolyzer cell can be used for other purposes, such as extraction of metal from ore and electroplating. In conventional electrolyzers, electrical energy is lost in the electrolysis reaction driving the diffusion of ions through the electrolyte and across the distance between the electrodes. Also, the ability to conduct electrolysis at higher temperatures would improve the efficiency of the electrolysis. However, at higher temperatures, electrolyzers face similar thermal stresses and cracking caused by differences in coefficients of thermal expansion between components of the solid oxide electrolyzer cell. Accordingly, better matching of coefficients of thermal expansion and lower operating temperatures are desired for electrolyzer cells.

A lambda sensor is a device typically placed in the exhaust stream of an internal combustion engine to measure the concentration of oxygen. That measurement allows regulation of the richness or leanness of the fuel/air mixture flowing into the engine. If the fuel/air stream contains too much oxygen, the quantity $\lambda$ is greater than 1, and the mixture is too lean. If the fuel/air stream contains too little oxygen, then $\lambda<1$ and the mixture is too rich. $\lambda$ equals 1, the ideal situation, when the mixture contains a stoichiometrically equivalent concentration of oxygen and hydrocarbon to allow for complete combustion. A lambda sensor positioned in the exhaust stream detects the amount of oxygen in the combustion products, thereby providing feedback regarding richness or leanness. Lambda sensors and other sensors rely on the diffusion of oxygen anions ($O^{2-}$) and other ions through barrier materials in ways similar to the manner in which oxygen anions diffuse through a solid electrolyte of a solid oxide fuel cell. Moreover, given the high operating temperature of lambda sensors and similar devices, sensors face thermal stresses, cracking, and delamination issues similar to those facing fuel cells and electrolyzers. Accordingly, embodiments of the present invention provide for improved sensor technology by addressing ionic conductivity and mismatching of coefficients of thermal expansion, among other reasons.

It has recently been reported that adjacent atomically flat layers of strontium titanate (STO) with yttria-stabilized zirconia (YSZ) produce an interface that has a dramatically higher ionic conductivity for oxygen anions. J. Garcia-Barriocanal et al., "Colossal Ionic Conductivity at Interfaces of Epitaxial $ZrO_2$:$Y_2O_3$/$SrTiO_3$ Heterostructures," 321 SCIENCE 676 (2008). Those authors concluded that growing thin epitaxial layers of YSZ on epitaxial STO caused the YSZ to conform under strain to the crystal structure of the STO, thereby creating voids in the YSZ crystal structure at the interface between the two materials. Those voids allowed an increase of oxygen ionic conductivity of approximately eight orders of magnitude relative to bulk YSZ at 500 K (227° C.). However, epitaxially-grown STO and YSZ require an extraordinarily clean environment and a relatively small scale, in addition to expensive deposition equipment. Furthermore, the geometries of establishing ionic communication between an electrode and an interface present another obstacle: the region for harvesting ions at the intersection of three materials (electrode, STO, and YSZ, for example) is by definition small compared to the contact area possible between an electrode and an electrolyte.

In view of the foregoing problems and disadvantages associated with the high operating temperatures of solid oxide cells, it would be desirable to provide solid oxide cells that can demonstrate lower operating temperatures. In addition, providing solid oxide cells and components that better tolerate higher temperatures would be advantageous. Moreover, the efficiency losses due to the thickness of electrolytes make thinner electrolytes desirable. Furthermore, it is also desirable to construct metal oxide electrolytes having dramatically higher ionic conductivities. Large-scale production of metal oxide electrolytes would be facilitated if higher ionic conductivities could be achieved without requiring epitaxial growth of electrolyte materials. It would be advantageous, also, if the geometry of harvesting ions at the intersection of electrode and electrolyte materials could be addressed.

SUMMARY OF THE INVENTION

It has been reported by the Applicants and colleagues in PCT Application No. PCT/US2011/024242, published on Aug. 18, 2011, as WO 2011/100361, and entitled, "LOW TEMPERATURE ELECTROLYTES FOR SOLID OXIDE CELLS HAVING HIGH IONIC CONDUCTIVITY," that an electrolyte of a solid oxide cell can be engineered to address some of the problems and shortcomings associated with solid oxide cells. In addition, Applicants have reported, in U.S. Provisional Patent Application No. 61/736,643 filed on Dec. 13, 2012, and entitled, "LAYERED ELECTROLYTES AND MODULES FOR SOLID OXIDE CELLS," further invention relating to, among other developments, methods for fabricating metal oxide electrolytes for use in solid oxide cells that do not require painstaking epitaxial growth of electrolyte materials. The disclosure of the '242 PCT application and of the '643 provisional application are incorporated herein by reference in their entirety. Here, Applicants report further unexpected developments of this technology.

Some embodiments of the present invention relate to electrolytes for solid oxide cells, comprising: at least one interface between an yttria-stabilized zirconia material and a glass material. Other embodiments relate to electrolytes for solid oxide cells, comprising: a first interface between an yttria-stabilized zirconia material and a glass material, and a second interface between a platinum oxide material and the yttria-stabilized zirconia material.

Further embodiments relate to solid oxide cells comprising: an electrolyte comprising an interface between an yttria-stabilized zirconia material and a glass material adapted to allow ionic conductivity along the interface; a first electrode in ionic communication with the interface of the electrolyte; and a second electrode in ionic communication with the interface of the electrolyte; wherein the first electrode and second electrode are electrically isolated from each other and are in ionic communication with each other via the interface. In the present application, when an electrode is "in ionic communication" with an electrolyte, for example, it means that it is possible for ions to pass between the electrode and the electrolyte at a cell operating temperature, provided that the cell is connected to an external circuit, suitable materials such as oxygen and hydrogen are fed to the electrodes of the cell, and the cell is otherwise configured for operation.

Certain embodiments of the present invention provide solid oxide cells comprising: an electrolyte comprising a first interface between an yttria-stabilized zirconia material and a glass material, and a second interface between a platinum oxide material and the yttria-stabilized zirconia material;

a first electrode in ionic communication with the electrolyte; and a second electrode in ionic communication with the electrolyte;

wherein the first electrode and second electrode are electrically isolated from each other and are in ionic communication with each other via the electrolyte.

Certain other embodiments relate to solid oxide cells comprising:

a plurality of substantially-planar substrates separated by a plurality of spacer elements; each substrate having a first side opposite a second side, and comprising an electrolyte disposed on the first side, the second side, or a combination thereof, a plurality of first electrodes disposed on the substrates in ionic communication with the electrolyte; a plurality of second electrodes disposed on the substrates in ionic communication with the electrolyte and electrically isolated from the plurality of first electrodes; wherein the plurality of substrates and the plurality of spacer elements define a plurality of first passages in fluid communication with the first electrodes and a plurality of second passages in fluid communication with the second electrodes.

Additional embodiments relate to methods of making a solid oxide cell, comprising: applying a first metal compound to a substrate, and exposing the first metal compound to an environment that will convert at least some of the first metal compound to a first metal oxide, thereby forming a substrate having electrolyte;

at least partially assembling the cell to comprise a plurality of the substrates having electrolyte, wherein the plurality of substrates are separated by a plurality of spacer elements;

applying an electrode composition to the substrates, wherein the electrode composition comprises a conductive particle and a second metal compound that is alike or different than the first metal compound, and exposing the second metal compound to an environment that will convert at least some of the second metal compound to a second metal oxide that is alike or different than the first metal oxide, thereby forming electrodes on the substrates, wherein the electrodes are in ionic communication with the electrolyte;

thereby forming the solid oxide cell.

Yet additional embodiments relate to methods of operating a solid oxide cell that comprises a first electrode and a second electrode, electrically isolated from each other and in ionic communication with an electrolyte, the methods comprising: contacting at least one of the electrodes with an ion-conducting species.

Still other embodiments relate to methods of operating a solid oxide cell as a fuel cell, which cell comprises an electrolyte comprising at least one interface between an yttria-stabilized zirconia material and a glass material, a first electrode and a second electrode electrically isolated from each other and in ionic communication with the electrolyte, the method comprising:

connecting the first electrode in electrical communication to an external circuit;

connecting the second electrode in electrical communication to the external circuit;

providing an oxygen-containing fluid such as a gas to the first electrode;

providing a fuel-containing fluid such as a gas to the second electrode; and heating or maintaining the cell to a temperature at which the cell provides electrical energy to the external circuit.

Those and other embodiments will be described in further detail herein.

BRIEF DESCRIPTION OF THE DRAWINGS

The figures are not necessarily to scale, and should not be construed as limiting. Some details may be exaggerated to aid comprehension.

DETAILED DESCRIPTION

Figure 1:
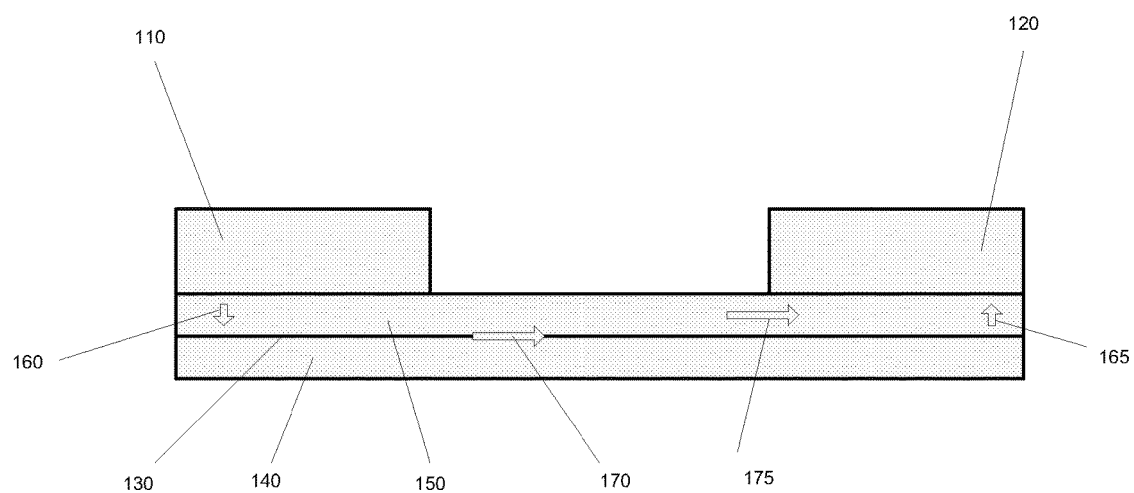
FIG. 1 depicts schematically one embodiment of the invention comprising a cathode (110), an anode (120), and electrolyte comprising an interface (130) between a yttria-stabilized zirconia material (150) and a glass material (140).

As required, detailed embodiments of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Solid Oxide Cells and Solid Oxide Fuel Cells

Some embodiments of the present invention provide solid oxide cells that exhibit enhanced performance relative to previous technologies. Enhanced performance may include one or more of increased ionic conductivity, lower operating temperature, mechanical stability for example at the microscopic level, increased electrical power output per mass or volume, and versatile and adaptable cell design. Applicants have unexpectedly found that a combination of materials, preparation techniques, and cell geometries have yielded surprisingly versatile solid oxide cells that are robust, scalable, and can be harnessed in large numbers for greater power, in some embodiments of the present invention.

Certain embodiments of the present invention take advantage of an unexpectedly successful combination of ionic diffusion through bulk metal oxide electrolyte, with ionic diffusion along an interface between two metal oxide materials or between a metal oxide material and a glass material. Ionic diffusion through the bulk of a metal oxide having one or more of an acceptable ionic conductivity at a given temperature, thickness, coefficient of thermal expansion, and other properties, allows a larger number of ions to enter and leave an electrolyte compared to the flux of ions entering an interface only. Once in the metal oxide, the ions can reach the interface that exhibits dramatically increased ionic conductivity. This advantageously affords a greater current density, lower operating temperature, smaller cell size, lower cost, greater simplicity of manufacture, or a combination of such advantages, in some embodiments of the present invention.

Other embodiments enjoy the advantage of there being no need for an interconnect. Because high temperature cells require ceramic electrodes, expensive interconnects are required to harvest the electricity from the electrodes. Interconnects face coefficient of thermal expansion issues, as do all components of high temperature cells. Some examples of the present invention provide electrodes and low temperature operation that eliminate the need for interconnects and overcome coefficient of thermal expansion mismatches that shorten the operating life of high temperature cells. Interconnects, in some cases, represent half the cost of a high temperature solid oxide fuel cell.

Certain embodiments of the present invention provide enhanced ionic conductivity through the metal oxide electrolyte, thereby allowing a lower operating temperature. By lowering the operating temperature of a solid oxide cell, less exotic and easier-to-fabricate materials can be utilized in the construction of the cell leading to lower production costs. Thus, some embodiments of the present invention provide solid oxide cells and components thereof employing simpler, less-expensive materials than the current state of the art. For example, if the operating temperature of a solid oxide cell can be lowered, then metals can be used for many different components such as electrodes and interconnects. At these lower operating temperatures, metals have more desirable mechanical properties, such as higher strength, than ceramics. In addition, this higher strength can allow metal components also to have a higher degree of porosity. Current ceramic electrode materials allow for porosity levels in the range of 30% to 40%. Incorporating higher porosity levels in ceramic materials renders them too structurally weak to support cell construction. However, through the use of certain metals or metal carbides, the porosity of an electrode can be provided in the higher range of 40% to 80% and yet retain sufficient mechanical strength for cell construction. Some embodiments of the present invention provide an electrode having a porosity ranging from about 40% to about 80%.

Lower production costs in addition to lower operating temperatures provide the opportunity for solid oxide cells to find application in a wider variety of fields. Additionally, lower operating temperatures reduce degradative processes such as those associated with variances in coefficients of thermal expansion between dissimilar components of the cell. Accordingly, some embodiments provide means and methods for reducing a degradation process in a solid oxide cell.

Still other embodiments produce a desirable surface catalytic effect. For example, by using the process of some embodiments of the present invention, thin films of metal oxides and pure metals (or other metal compounds) can be formed on the exposed pore surfaces of electrodes to produce more chemically active sites at triple phase boundaries where either fuel-gas (as in the case of the anode electrode) or gaseous oxygen (as in the case of the cathode electrode) come into contact with the solid (yet porous) electrodes in a fuel cell.

Other embodiments provide methods of making solid oxide cells and components thereof. Certain embodiments provide methods of making solid oxide cells and components thereof applying temperatures dramatically below those of current methods. Current methods of making solid oxide fuel cells involve the sintering of ceramic and/or metal powders. High sintering temperatures during fabrication of various components, such as the electrolyte, can compound problems associated with variances in coefficients of thermal expansion. For example, high sintering temperatures can also accelerate grain growth (as can high operating temperatures), reducing ionic conductivity.

As used herein, "solid oxide cell" means any electrochemical cell that contains a metal oxide electrolyte, and refers to, for example, solid oxide fuel cells, solid oxide electrolyzer cells, cells that can operate as a fuel cell and an electrolyzer cell, and solid oxide sensors.

An "electrolyte" is a material capable of allowing ions to flow between electrodes. Without wishing to be bound by theory, it is believed that certain materials allow ionic conductivity at interfaces between materials. Thus, a material functions as an electrolyte if it conducts ions through the bulk of the material, along interfaces of the material such as grain boundaries or where one material contacts another material, or a combination of such methods. The mode of ionic conductivity is not limited for electrolytes of the present invention. "Metal oxide electrolyte" indicates a material, useful as an electrolyte in a solid oxide cell, which contains a metal oxide. The metal oxide electrolyte can contain one or more metal oxides dispersed in any suitable manner. For example, two metal oxides can be mixed together in the manner of $ZrO_2:Y_2O_3$, or $SrTiO_3$. For another example, two metal oxides can be present in discrete domains having an abrupt interface between them. In yet another example, two metal oxides can form a diffuse interface between them. Still further examples provide more than two metal oxides present in a metal oxide electrolyte, such as, for example, $ZrO_2:Y_2O_3/SrTiO_3$. The metal oxide electrolyte optionally further contains a material other than a metal oxide. Examples include, but are not limited to, metals, semiconductors, insulators (other than metal oxides), carbides, nitrides, phosphides, sulphides, and polymers, and combinations thereof. In the context of this disclosure, silicone polymers are polymers, while silica is a metal oxide. When used in this document, the meaning of "material" includes metal oxides unless otherwise indicated.

An interface means a region in which two materials meet. As mentioned above, the interface can be abrupt, or it can be diffuse. Or an interface can have a variable physical character, in some locations more abrupt, even at the atomic level, and in other locations rougher, or even diffuse. In some cases, a concentration gradient of one material can be seen in the other material. For example, at least one interface between an yttria-stabilized zirconia material and a glass material indicates, in some cases, that yttria-stabilized zirconia contacts a glass substrate. The interface can be abrupt, diffuse, or a combination thereof.

A metal oxide material, in certain embodiments, can comprise, among other things, amorphous material, crystalline material, nanocrystalline material, and combinations thereof. Crystalline material includes single crystals and material that has been formed epitaxially, such as by atomic layer deposition.

Any suitable yttria-stabilized zirconia material can be used, in certain embodiments of the present invention. In some instances, the yttria-stabilized zirconia material is made by depositing zirconium metal compounds and yttria metal compounds on the substrate, and exposing the metal compounds to an environment that will convert at least some of the metal compounds to metal oxides.

Certain embodiments relate to platinum oxide materials being proximal to the yttria-stabilized zirconia material. Proximal means near or touching. Thus, a platinum oxide material can contact the yttria-stabilized zirconia material, or another material can be interposed between the two. For example, in some cases, interfacial catalysts can be included. The electrolyte can provide ionic communication with electrodes in any suitable manner. For example, in some cases, an yttria-stabilized zirconia material is in ionic communication with an electrode. In other cases, it can be demonstrated that an interface formed by the electrolyte, such as between an yttria-stabilized zirconia material and a glass material, provides ionic communication with an electrode. Still other cases provide an electrolyte that further comprises a platinum oxide material in ionic communication with a first electrode, a second electrode, or both.

Some embodiments employ no oxide other than yttria-stabilized zirconia on glass as the electrolyte. Other embodiments employ no oxide other than platinum oxide on yttria-stabilized zirconia on glass as the electrolyte. Certain embodiments specifically exclude strontium titanate from the electrolyte, as Applicants have unexpectedly found embodiments working without that material.

Meanwhile, other embodiments of the present invention provide at least one metal oxide chosen from strontium titanate, titania, alumina, zirconia, yttria-stabilized zirconia, alumina-doped yttria-stabilized zirconia, iron-doped zirconia, platinum oxide, magnesia, ceria, samarium-doped ceria, gadolinium-doped ceria, and combinations thereof. In other embodiments, the metal oxide is chosen from alumina, titania, zirconia, yttria-stabilized zirconia, alumina-doped yttria-stabilized zirconia, iron-doped zirconia, magnesia, ceria, samarium-doped ceria, gadolinium-doped ceria, and combinations thereof.

Yttria-stabilized zirconia useful in certain embodiments of the present invention can contain yttria and zirconia in any suitable ratio. For example, some additional embodiments provide yttria-stabilized zirconia comprising from about 0.5 mol % to about 2 mol % yttria, from about 1 mol % to about 5 mol % yttria, from about 5 mol % to about 10 mol % yttria, from about 10 mol % to about 20 mol % yttria, from about 12 mol % to about 18 mol % yttria, or from about 14 mol % to about 16 mol % yttria. In one embodiment, a metal oxide suitable for one or more layers of an electrolyte comprises zirconium oxide ($ZrO_2$) or yttria-stabilized zirconia (YSZ) $Zr_{(1-x)}Y_xO_{[2-(x/2)]}$, x=0.08-0.20, or 0.10-0.50, or 0.15-0.20, in certain embodiments.

Platinum oxides useful in some embodiments of the present invention include any suitable platinum oxides, or oxides containing platinum ions. $PtO_2$, PtO, and $Pt_3O_4$ (platinum (II, IV) oxide) and combinations thereof, can be used in certain cases.

Metal oxides suitable for use in air electrodes, fuel electrodes, electrolyzer electrodes, sensors, and/or electrolytes, in addition to the materials recited hereinabove, can be chosen from $CeO_2$—$ZrO_2$ wherein $CeO_2$ is about 10-90 weight percent; yttria-stabilized zirconia (YSZ) wherein yttria is present in an amount of about 1-50 mol percent; $CeO_2$—$PrO_2$ wherein $PrO_2$ is up to about 50 weight percent; $PrO_2$—$CeO_2$—$ZrO_2$ wherein $PrO_2$—$CeO_2$ is up to about 90 weight percent; $PrO_2$—$ZrO_2$ wherein $PrO_2$ is 10 to 90 weight percent; scandia-doped zirconia (SSZ) doped with one or more of $Co_3O_4$, $Bi_2O_3$, $SiO_2$, $TiO_2$, $Fe_2O_3$, NiO, $MnO_2$, $CeO_2$, and $Al_2O_3$; YSZ doped with one or more of $Co_3O_4$, $Bi_2O_3$, $SiO_2$, $TiO_2$, $Fe_2O_3$, NiO, $MnO_2$, $CeO_2$, and $Al_2O_3$; CaO stabilized zirconia doped with one or more of $Co_3O_4$, $Bi_2O_3$, $SiO_2$, $TiO_2$, $Fe_2O_3$, NiO, $MnO_2$, $CeO_2$, and $Al_2O_3$; mixed LSM and YSZ; and combinations thereof.

Metal oxides of the following elements can be used in embodiments of air electrodes, fuel electrodes, electrolyzer electrodes, sensors, and/or electrolytes in some embodiments of the present invention: lithium, beryllium, sodium, magnesium, aluminum, silicon, potassium, calcium, scandium, titanium, vanadium, chromium, manganese, iron, cobalt, nickel, copper, zinc, gallium, germanium, arsenic, bromine, rubidium, strontium, yttrium, zirconium, niobium, molybdenum, technetium, ruthenium, rhodium, palladium, antimony, tellurium, silver, cadmium, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, irridium, gold, mercury, thallium, lead, bismuth, radium, actinium, platinum, thorium, protactinium, uranium, neptunium, plutonium, americium, berkelium, californium, einsteinium, fermium, mendelevium, nobelium, lawrencium, or curium. Oxides containing more than one of the foregoing elements, and oxides containing elements in addition to the foregoing elements, also can be used in embodiments of the present invention.

In some embodiments, detection of a given material need not require crystallographic analysis. For example, alumina-doped yttria-stabilized zirconia refers to oxide material comprising aluminum, yttrium, zirconium, and oxygen. Accordingly, detection of constituent elements signifies the indicated material. Elemental detection methods are widely known, and include, but are not limited to, flame emission spectroscopy, flame atomic absorption spectroscopy, electrothermal atomic absorption spectroscopy, inductively coupled plasma spectroscopy, direct-current plasma spectroscopy, atomic fluorescence spectroscopy, and laser-assisted flame ionization spectroscopy.

Electrolytes of solid oxide cells, according to some embodiments of the present invention, comprise a plurality of nanocrystalline grains, the nanocrystalline grains comprising one or more of the metal oxides that are suitable for use as an electrolyte in a solid oxide cell. In some embodiments, the nanocrystalline grains have an average size of less than about 50 nm. In other embodiments, nanocrystalline grains of electrolyte layers have an average size ranging from about 2 nm to about 40 nm or from about 3 nm to about 30 nm. In another embodiment, nanocrystalline grains have an average size ranging from about 5 nm to about 25 nm. In a further embodiment, nanocrystalline grains have an average size less than about 10 nm or less than about 5 nm.

Electrolytes of solid oxide cells are substantially non porous, in some embodiments. In one embodiment, an electrolyte has a porosity less than about 20%. In another embodiment, an electrolyte has a porosity less than about 15% or less than about 10%. In a further embodiment, an electrolyte has a porosity less than about 5% or less than about 1%. In one embodiment, an electrolyte is fully dense meaning that the electrolyte has no porosity.

In some embodiments, an electrolyte has a thickness ranging from about 1 nm to about 1 mm or from about 10 nm to about 500 μm. In other embodiments, an electrolyte has a thickness ranging from about 2 nm to about 25 nm, from about 5 nm to about 50 nm, from about 50 nm to about 250 nm, from about 100 nm to about 1 μm, or from about 500 nm to about 50 μm. In another embodiment, an electrolyte has a thickness ranging from about 750 nm to about 10 μm, or from about 1 μm to about 5 μm, or from about 1.2 μm to about 4 μm, or from about 1.5 μm to about 2 μm. In a further embodiment, an electrolyte has a thickness less than about 10 μm or less than about 1 μm. In one embodiment, an electrolyte has a thickness ranging from about 1 nm to about 100 nm or from about 50 nm to about 100 nm. In another embodiment, an electrolyte has a thickness ranging from about 1 nm to about 10 nm or from about 5 nm to about 50 nm. Certain embodiments provide an electrolyte having a thickness greater than about 1 nm, greater than about 5 nm, greater than about 10 nm, greater than about 25 nm, greater than about 50 nm, greater than about 100 nm, greater than about 150 nm, or greater than about 200 nm. In still other embodiments, an electrolyte has a thickness greater than about 500 µm.

When the electrolyte has two or more layers of metal oxide material, the thickness of each layer is not limited. In some cases, the thickness of a given layer of metal oxide material is at least about 1 nm, at least about 2 nm, at least about 5 nm, at least about 10 nm, at least about 20 nm, at least about 50 nm, or at least about 100 nm. In other cases, the thickness of a given layer of metal oxide material is less than about 100 nm, less than about 50 nm, less than about 20 nm, less than about 10 nm, less than about 5 nm, or less than about 2 nm.

Any suitable substrate can be used in certain embodiments of the present invention. Certain embodiments provide a substrate in the form of a thin sheet. In some of those embodiments, the substrate comprises at least one thin sheet. Thin sheets of material, such as, for example, glass, mica, metal oxides, conductors, semiconductors, and insulators, can be used. Some embodiments employ thin sheets of $SiO_2$, MgO, $BaTiO_3$, NaCl, KCl, alone or in combination. Also, thin sheets are chosen from crystalline material such as slices of single crystal and epitaxial films grown on a substrate and optionally removed from that substrate. Other materials that can be used provide a thin sheet that can withstand the temperatures of processing and operation, such as high temperature polymers, for example polyamides. Fused silica glass, soda-lime glass, sodium borosilicate glass, among others, may also be used as a substrate.

A substrate, in some embodiments, is pretreated prior to application of the metal compound composition. In some cases, the substrate is cleaned according to any suitable method, such as a surfactant-assisted wash (e.g., soap and water), or rinsed with a solvent such as water, lower alkyl alcohols, organic hydrophobic solvents, or solvents present in metal compound compositions, or combinations thereof. In one embodiment, for example, the substrate can be etched according to known methods, for example, with an acid wash comprising nitric acid, sulphuric acid, hydrochloric acid, phosphoric acid, or a combination thereof, or with a base wash comprising sodium hydroxide or potassium hydroxide, for example. In another embodiment, the substrate is polished, with or without the aid of one or more chemical etching agents, abrasives, and polishing agents, to make the surface either rougher or smoother. In a further embodiment, the substrate is pretreated such as by carburizing, nitriding, plating, or anodizing.

Some embodiments relate to an electrolyte having at least one region adapted to allow ionic conductivity through bulk electrolyte material. In some cases, such a region is proximal to at least one electrode. Thus, still other embodiments provide electrolytes having a first region adapted to allow ionic conductivity through bulk electrolyte material, wherein the first region is proximal to a first electrode; and a second region adapted to allow ionic conductivity through bulk electrolyte material, wherein the second region is proximal to a second electrode; wherein the first region is separated from the second region by the at least one interface.

Certain embodiments provide an electrode in proximity to yttria-stabilized zirconia to facilitate oxygen ion diffusion into the electrolyte. Other embodiments employ electrodes that integrate with one or more interfaces between the layers of the electrolyte. Any suitable method allowing electrode-interface contact and ionic communication can be used. For example, the electrolyte can be formed on the substrate, and then the electrolyte can be selectively etched, exposing one or more of the interfaces. Any suitable means for etching can be employed, such as, for example, a diamond scribe, a laser, a molecular ion beam, or a combination thereof can be employed to expose the interfaces. Then, the electrode can be added or formed in the exposure as described herein. Accordingly, in further embodiments of the present invention, an interface is adapted to allow ionic conductivity along the interface. That means the interface is present in the cell so that ions passing from an electrode or bulk electrolyte can propagate along the interface during cell operation.

Further embodiments of the present invention provide one or more mechanisms by which ions move through the electrolyte. Without wishing to be bound by theory, it is believed that the enhanced performance of the solid oxide cells in certain embodiments of the present invention is due to increased ionic conductivity in the inventive electrolytes. And it is believed that the increased ionic conductivity is primarily interfacial conductivity. That is, oxygen ion conductivity along the interface between two different materials explains the improved performance of the cell. It is believed, for example, that forming a thin layer of yttria-stabilized zirconia material on glass causes strain in the YSZ, facilitating ionic conduction along the interface of the two materials. Thus, in some embodiments, the electrolyte is adapted to allow ionic conductivity along one or more interfaces between two different materials. In other embodiments the electrolyte is further adapted to allow ionic conductivity through the bulk of one or more metal oxide materials.

As stated above, some embodiments of the present invention provide electrolytes, and methods of making and using the same.

Some embodiments of the present invention include electrolytes and methods for making electrolytes having enhanced ionic conductivity. Ionic conductivity is the rate at which one or more ions move through a substance. Ionic conductivity generally depends upon temperature in most solid electrolytes, and is usually faster at higher temperature. In some cases, poor ionic conductivity at room temperature prevents economical use of certain fuel cell technologies. Accordingly, enhancing ionic conductivity can provide either more efficient solid oxide cell operation at a given temperature, or operation at a lower temperature that is thereby rendered efficient enough to be economically feasible.

Ionic conductivity can relate to any ionic conductivity, such as, for example, the conductivity of monoatomic, diatomic, and multiatomic ions; monovalent, divalent, trivalent, tetravalent, and other multivalent ions; cations; anions; solvated and partially-solvated ions, and combinations thereof. In some embodiments, ionic conductivity concerns the conductivity of $O^{2-}$. In other embodiments, ionic conductivity concerns the conductivity of $O^{2-}$, $H^+$, $H_3O^+$, $OH^-$, $NH_4^+$, $Li^+$, $Na^+$, $K^+$, $Mg^+$, $Ca^+$, $F^-$, $Cl^-$, $Br^-$, $I_3^-$, $I^-$, and combinations thereof. Ionic conductivity is often reported in units of 1/(ohms cm) or S/cm, where 1 S=1 A/V. In context of the present invention, ionic conductivity is enhanced if, in reference to a literature or experimental value of bulk ionic conductivity of the most-ionic conductive material in the metal oxide electrolyte, the ionic conductivity has increased by a statistically significant amount. In some embodiments, the ionic conductivity has increased at least one order of magnitude, from about one order of magnitude to about two orders of magnitude, from about two orders of magnitude to about three orders of magnitude, from about three orders of magnitude to about four orders of magnitude, from about four orders of magnitude to about five orders of magnitude, from about five orders of magnitude to about six orders of magnitude, from about six orders of magnitude to about seven orders of magnitude, from about seven orders of magnitude to about eight orders of magnitude, from about eight orders of magnitude to about nine orders of magnitude, from about nine orders of magnitude to about ten orders of magnitude, or greater than about ten orders of magnitude.

Yet additional embodiments provide electrolytes having one or more interfacial catalysts. Any suitable interfacial catalyst in any suitable form can be included in or on the electrolytes, or for example, where the electrolytes and electrodes contact each other. For example, one or more interfacial catalysts can be disposed where the electrolyte is in ionic communication with one or more of the first electrodes, one or more of the second electrodes, or a combination thereof. In some cases, interfacial catalysts are chosen from Li, Ti, Cr, Mn, Fe, Co, Ni, Sr, Sn, Ce, Sm, Gd, Na, K, Cl, and combinations of two or more thereof. They can be present in any suitable form, such as, for example, metal oxides, metal nanopowders, or a combination thereof.

Electrodes, electrolytes, or both, comprising interfacial catalysts can additionally demonstrate compositional gradients based on the distribution of the interfacial catalysts in the electrodes and electrolytes. In one embodiment, an electrolyte is formed on a substrate and comprises a plurality of metal oxide layers disposed on the substrate, and an electrode is formed on the electrolyte, wherein metal oxide layers closer to the electrode comprise greater amounts of catalytic material such as interfacial catalysts than metal oxide layers further from the electrode. Moreover, in another embodiment, metal oxide layers further from the substrate comprise greater amounts of catalytic material such as interfacial catalysts than metal oxide layers closer to the substrate. In one embodiment, for example, metal oxide layers further from the substrate comprise about 5 weight percent catalytic material while metal oxide layers closer to the substrate comprise about 1 weight percent catalytic material.

Catalytic sites can be formed by any suitable method. One method involves forming the corresponding metal oxide by applying a metal compound, heating in air at 450° C., and thereby forming the metal oxide. Then, the metal oxide is reduced by any suitable method. For example, platinum oxide can be reduced to form metallic platinum by baking in an Ar/H$_2$ atmosphere at 600° C. for 15 minutes.

Some additional embodiments provide solid oxide cells having electrolytes that have a first interface between an yttria-stabilized zirconia material and a glass material, and a second interface between a platinum oxide material and the yttria-stabilized zirconia material. Other additional embodiments have solid oxide cells having electrolytes comprising an interface between an yttria-stabilized zirconia material and a glass material adapted to allow ionic conductivity along the interface; a first electrode in ionic communication with the interface of the electrolyte; and a second electrode in ionic communication with the interface of the electrolyte; wherein the first electrode and second electrode are electrically isolated from each other and are in ionic communication with each other via the interface.

Electrical isolation means that electricity, such as the flow of electrons, cannot pass between, for example, the first electrode and the second electrode, via metallic electrical conduction. A first electrode and a second electrode remain in electrical isolation if the only route of electrical communication between them requires electricity to flow through an external circuit.

Still other instances of the present invention relate to solid oxide cells comprising: an electrolyte comprising a first interface between an yttria-stabilized zirconia material and a glass material, and a second interface between a platinum oxide material and the yttria-stabilized zirconia material; a first electrode in ionic communication with the electrolyte; and a second electrode in ionic communication with the electrolyte; wherein the first electrode and second electrode are electrically isolated from each other and are in ionic communication with each other via the electrolyte.

In some cases, one or more ion-conducting species can contact the first electrode, the second electrode, or both. Without wishing to be bound by theory, Applicants have observed dramatic improvement in cell performance by contacting the cathodes or oxygen electrodes of cells with ion-conducting species such as water, salt water, and dried salt water, i.e. NaCl. Cells have been observed to generate electrical potential and electrical current at room temperature upon introduction of moisture or salt water where no significant electrical energy was detected in the absence of the moisture or salt water. Then, significant cell performance continued after the salt water dried. It is believed that an ion-conducting species improves ionic conductivity between an electrode and an electrolyte. Any suitable ion-conducting species can be used. To operate as an ion-conducting species, a liquid should have the ability to transport ions, and can be hydrophilic or hydrophobic. In specific cases, the ion-conducting species is hydrophilic. Certain embodiments allow the ion-conducting species to be chosen from water, salt water, an ionic liquid, an inorganic salt, and combinations of two or more thereof. A combination of water and salt water is diluted salt water. In one embodiment, the ion-conducting species is about 1%, about 3%, about 5%, about 10%, about 25%, or about 35% NaCl in water by weight, or it can be saturated aqueous NaCl solution. Ionic liquids, comprising cations and anions that form a composition that is liquid at the operating temperature of the cell, can include any suitable ionic liquid. In some cases, the ion-conducting species comprises tetrafluoroborate. In other cases, the ion-conducting species is an ionic liquid comprising tetrafluoroborate. Still other cases provide an inorganic salt such as, for example, alkali metal halide salts, alkaline earth halide salts, sulfates, nitrates, phosphates, permanganates, and combinations thereof. NaCl, KCl, and potassium permanganate, alone or in combination, also can be used. Suitable cations and anions for ion-conducting species are not limited. Certain embodiments allow a higher operating temperature when the ion-conducting species is chosen from those that can withstand higher temperatures, such as, for example, inorganic salts and suitable ionic liquids. Similarly, suitable ionic liquids are not limited. See, for example, S. Zhang et al., "Physical Properties of Ionic Liquids: Database and Evaluation," J. Phys. Chem. Ref. Data, Vol. 35, No. 4, pp. 1475-1517 (2006), which is incorporated herein by reference. As reported by Zhang et al., several ionic liquids have a melting point below room temperature (72° F., about 22° C., about 295 K), and several just above. Table 1 lists a few ionic liquids and their melting point.

TABLE 1

Melting Temperature of Select Ionic Liquids

| Zhang Cation Reference | Cation | Zhang Anion Reference | Anion | Tm (K) |
|---|---|---|---|---|
| 203 | EMI | 021 | BF$_4$ | 279.15-288.15 |
| 203 | EMI | 081 | AlCl$_4$ | 280.15 |
| 208 | C3MI | 021 | BF$_4$ | 256.15 |
| 216 | C5MI | 031 | TFSI | 264.15 |

TABLE 1-continued

Melting Temperature of Select Ionic Liquids

| Zhang Cation Reference | Cation | Zhang Anion Reference | Anion | Tm (K) |
|---|---|---|---|---|
| 229 | C8MI | 021 | $BF_4$ | 193.15 |
| 1101 | C4-py | 031 | TFSI | 299 |
| 1101 | C4-py | 021 | $BF_4$ | 288.45 |
| 1703 | $P1,10_3$ | 011 | Cl | 372.05 |
| 1703 | $P1,10_3$ | 011 | $Cl_w$ | 280.75 |
| 1703 | $P1,10_3$ | 012 | Br | 368.35 |
| 1703 | $P1,10_3$ | 012 | $Br_w$ | 269.35 |

EMI = 1-ethyl-3-methylimidazolium
C3MI = 1-propyl-3-methylimidazolium
C5MI = 1-pentyl-3-methylimidazolium
C8MI = 1-octyl-3-methylimidazolium
C4-py = n-butyl pyridinium
$P1,10_3$ = tridecylmethylphosphonium
TFSI = bis((trifluoromethyl)sulfonyl)imides Factors other than or in addition to melting temperature can be considered when selecting ionic liquids for use in the present invention. One or more of density, viscosity, surface tension, conductivity, polarity, and the electrochemical window of a given ionic liquid may be considered. See, e.g., Zhang et al. Other ionic liquids that can be used include, for example, 1,3-dimethylimidazolium tetrafluoroborate and 1,3-dimethylimidazolium methyl sulfate.

In certain instances, ionic liquids can be used in combination with other ionic liquids and/or with one or more solvents that liquefy a composition that would otherwise be solid or more viscous than desired at a given temperature. For example, as shown in the table above, tridecylmethylphosphonium halide salts exhibit a dramatic drop in melting temperature in the presence of water. For another example, aqueous solutions of ionic liquids can be constructed, such as reported in W. Liu et al., "The Physical Properties of Aqueous Solutions of the Ionic Liquid [BMIM][$BF_4$]", J. Solution Chem. 33:1337-1346 (2006), which is incorporated herein by reference.

Substantially-planar substrates can contain electrolyte on one planar side, or both planar sides. It can be said that one planar side is a first side, and the opposite planar side is a second side. One can appreciate that a greater power density can be achieved when both sides of a substantially-planar substrate contain electrolyte and electrodes that are electrically isolated from each other. Electrolyte can appear on the substrate in any suitable distribution, such as isolated domains, contiguous domains, porous coatings, and non-porous coatings.

The substantially-planar substrates can be separated by a plurality of spacer elements. Any suitable spacer elements can be used, such as, for example, ceramics, ceramic paper, glass, and glass capillary tubes, and combinations of two or more thereof. In certain embodiments, glass made to withstand high temperatures and with low coefficients of thermal expansion, such as Pyrex® glass (borosilicate glass, or similar glass containing oxides of silicon, boron, sodium, aluminum, and optionally iron, potassium, and/or calcium), or tempered soda-lime glass, in the form of flat spacers or capillary tubes, can be used. Capillary tubes can be used where it is desired to reduce the linear distance of electrolyte through which ions must travel, from one electrode to another, during the operation of the cell. Capillary tubes allow electrodes to approach within a millimeter or even a tenth of a millimeter of each other while remaining electrically isolated. Electrolyte separates the electrodes, in such cases, and provides ionic communication between the electrodes during cell operation.

In some cases, the plurality of substrates and the plurality of spacer elements define a plurality of first passages in fluid communication with the first electrodes and a plurality of second passages in fluid communication with the second electrodes. See, e.g., FIGS. 4 & 5. The plurality of first passages can be adapted to provide an oxygen-containing gas to the plurality of first electrodes. That means, in some cases, that the first passages are open to the air during cell operation. In other cases, a device such as a manifold, tubes, or a fan can provide air or other oxygen-containing gas to the first passages, under slight or significant pressure to push oxygen through the first passages to contact the first electrodes. Thus, certain embodiments provide an oxygen-containing gas input manifold sealably connected to the plurality of first passages. "Sealably" means the manifold or similar device allows the supply of gas or other fluid to the cell without substantial leakage of the fluid out of the manifold or cell, and without substantial leakage of ambient atmosphere or other fluid into the manifold or cell. Further embodiments provide an oxygen-containing gas exhaust manifold sealably connected to the plurality of first passages to collect the oxygen-containing gas that is somewhat depleted of oxygen, or the exhaust of the first passages could be open to the atmosphere. When the cell is operated as a fuel cell, the first electrodes would operate as cathodes where oxygen is reduced and oxygen anions pass into the electrolyte.

Similarly, the plurality of second passages can be adapted to provide a fuel-containing gas to the plurality of second electrodes. The fuel-containing gas can be any suitable fuel, such as, for example, hydrocarbons, hydrogen, or combinations thereof. In some embodiments, the fuel-containing gas comprises hydrogen. In other embodiments, the fuel-containing gas is hydrogen. In still other embodiments, the fuel-containing gas comprises natural gas, syngas, lower alkanes, and combinations thereof. Because fuel-containing gases such as hydrogen mixed with air can pose a risk for combustion, care should be taken in the provision of fuel-containing gases to the cell. When the cell is operated as a fuel cell, the second electrodes would operate as anions where the fuel is oxidized.

Certain embodiments of the present invention provide a solid oxide cell comprising a fuel gas input manifold sealably connected to the plurality of second passages, to allow fuel-containing gas to enter the cell and contact the second electrodes. Additional embodiments provide a fuel gas exhaust manifold sealably connected to the plurality of second passages. The fuel gas exhaust manifold would collect the fuel-containing gas, obviously with a lower concentration of fuel, and at least some of the byproducts of the reaction, such as water.

In some embodiments, the oxygen-containing gas input manifold comprises a device for applying an ion-conducting species to the plurality of first electrodes. In other embodiments, the device is independent of the manifold. Such a device can be adapted to provide a mist or aerosol of an ion-conducting species to the plurality of first electrodes. In other cases, the device is adapted to provide a bolus of ion-conducting species to the plurality of first passages. For example, it may be found advantageous for the operation of a particular cell to occasionally flush the first passages with an ion-conducting species, when it is perceived the ion-conducting species has evaporated or degraded. With fresh ion-conducting species thereby contacting the first electrodes, optimal cell operation can resume. In additional embodiments, the ion-conducting species is chosen so that it does not degrade or evaporate at the cell operating temperature, allowing longer operating time in between introduction of fresh ion-conducting species.

Once the metal oxide is formed, in some embodiments of the present invention, one or more epoxies can be applied to the metal oxide. In addition, or alternatively, epoxy can be applied to other components, such as one or more electrodes of the solid oxide cell. Epoxy can be used, in some embodiments of the present invention, to seal the solid oxide cell so that reactants from one side of the cell do not penetrate to the other side of the cell. Any suitable epoxy that can withstand the operating temperature of the solid oxide cell can be used alone or in combination. U.S. Pat. No. 4,925,886 to Atkins et al. discloses and claims epoxy compositions comprising two epoxies and having a usable temperature of at least 160° C., for example. U.S. Pat. No. 6,624,213 to George et al. reports tests of various epoxy compositions at 177° C., for further examples. The '886 patent and the '213 patent are incorporated by reference herein in their entireties.

Further embodiments provide a solid oxide cell in which the plurality of first electrodes and the plurality of second electrodes are adapted to connect in electrical communication to an external circuit. That means the cell can provide electrical energy or electricity to a circuit when the cell is operated as a fuel cell, or can receive electrical energy when operated as an electrolyzer, or can provide a signal when the cell is operated as a sensor.

Some embodiments of the present invention include a rig for mechanically supporting the plurality of substrates. The rig can be constructed of any suitable material, such as, for example, metal, plastic, glass, ceramic, cermet, and combinations thereof. In certain cases, the rig is made of metal, such as steel or aluminum, or alloys of either. The rig can be suitable for supporting, transporting, and operating a cell comprising a plurality of substantially-planar substrates, in some cases. The rig can further comprise at least one device for compressing the substantially-planar substrates in a direction normal to the plane of the substrates. By squeezing the substrates together, greater consistency in cell geometry results. Also, further embodiments provide a method of making the solid oxide cell that comprises assembling, in the rig, substantially-planar substrates coated on both sides with electrolyte, with each substrate separated from its neighbors by spacer elements. Then the device carefully squeezes the substrates together, and the rig and substrates are optionally heated to a temperature sufficient to bond the electrolyte and the spacer elements. In some instances, that temperature is just below the glass transition temperature of the spacer elements, if those spacer elements comprise glass. In other embodiments, the rig and substrates are heated to a temperature of up to about 450° C., up to about 550° C., up to about 650° C., or up to about 750° C. In other cases, a sealant such as a high temperature pipe thread sealant (McMaster) is added to the spacer element, and the assembled substrates are heated to a temperature sufficient to bond the sealant, such as, for example, 200° C. Thus, additional embodiments provide a rig having a device for compressing substrates that comprises a plate to contact a substrate and a turn screw to compress the substrates. Optionally, any suitable device such as a plunger, weight, spring loaded mechanism, can apply a compressive force in lieu of or in addition to a turn screw.

Additional methods of making a solid oxide cell form part of the present invention. Further embodiments relate to methods of making a solid oxide cell, comprising:
applying a first metal compound to a substrate, and exposing the first metal compound to an environment that will convert at least some of the first metal compound to a first metal oxide, thereby forming a substrate having electrolyte;
at least partially assembling the cell to comprise a plurality of the substrates having electrolyte, wherein the plurality of substrates are separated by a plurality of spacer elements;
applying an electrode composition to the substrates, wherein the electrode composition comprises a conductive particle and a second metal compound that is alike or different than the first metal compound, and
exposing the second metal compound to an environment that will convert at least some of the second metal compound to a second metal oxide that is alike or different than the first metal oxide, thereby forming electrodes on the substrates, wherein the electrodes are in ionic communication with the electrolyte;
thereby forming the solid oxide cell.

In some methods of the present invention, the substrate comprises glass. In other methods, the spacer elements comprise glass. In still other methods, the substrate is substantially planar, and is a glass plate or sheet, and the spacer elements are glass capillary tubes.

Certain embodiments relate to instances wherein the first metal compound comprises a zirconium metal compound. In addition, other methods relate to applying an yttrium metal compound with the first metal compound. The applying can be performed by any suitable method. Certain cases provide spin coating or dip coating a substrate or a plurality of substrates to apply a metal compound. A quantity of metal compound, optionally present in a metal compound composition with one or more solvents, is added to the substrate and spun for a sufficient time to yield a uniform liquid coating on the substrate, which is then heated to convert at least some of the metal compound into metal oxide. Dip coating allows a substrate or a plurality of substrates to be inserted or submerged in a bath of metal compound or metal compound composition and carefully removed to yield a uniform liquid coating on the substrate. The substrate is then subjected to an environment that will convert at least some of the metal compounds to metal oxides.

Applying one or more metal compounds to one or more materials can occur according to any suitable method. Dipping, spraying, brushing, mixing, spin coating, and combinations thereof, among other methods, can be used. A metal compound composition, in some embodiments, is applied to the substrate at a temperature less than about 250° C. In other embodiments, a metal compound, optionally present in a composition comprising one or more suitable solvents and optionally one or more additional metal compounds, is applied to the substrate at a temperature less than about 200° C., less than about 150° C., less than about 100° C., or less than about 50° C. In a further embodiment, a metal compound composition is applied to the substrate at room temperature. An additional embodiment provides a metal compound composition applied at less than about room temperature. Then the metal compound is converted to form at least one metal oxide. In certain embodiments, the metal compound is fully converted to a metal oxide.

In some embodiments, the metal compound is chosen from a metal carboxylate, a metal alkoxide, a metal β-diketonate, or a combination thereof.

A metal carboxylate comprises the metal salt of a carboxylic acid, e.g., a metal atom and a carboxylate moiety. In some embodiments of the present invention, a metal salt of a carboxylic acid comprises a transition metal salt. In other embodiments, a metal salt of a carboxylic acid comprises a rare earth metal salt. In a further embodiment, metal carboxylate compositions comprise a plurality of metal salts of carboxylic acids. In one embodiment, a plurality of metal salts comprises a rare earth metal salt of a carboxylic acid and a transition metal salt of a carboxylic acid.

Metal carboxylates can be produced by a variety of methods known to one skilled in the art. Non-limiting examples of methods for producing the metal carboxylate are shown in the following reaction schemes:

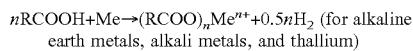
nRCOOH+Me→(RCOO)$_n$Me$^{n+}$+0.5nH$_2$ (for alkaline earth metals, alkali metals, and thallium)

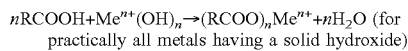
nRCOOH+Me$^{n+}$(OH)$_n$→(RCOO)$_n$Me$^{n+}$+nH$_2$O (for practically all metals having a solid hydroxide)

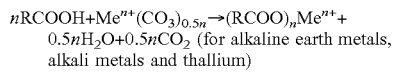
nRCOOH+Me$^{n+}$(CO$_3$)$_{0.5n}$→(RCOO)$_n$Me$^{n+}$+ 0.5nH$_2$O+0.5nCO$_2$ (for alkaline earth metals, alkali metals and thallium)

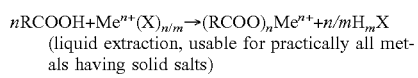
nRCOOH+Me$^{n+}$(X)$_{n/m}$→(RCOO)$_n$Me$^{n+}$+n/mH$_m$X (liquid extraction, usable for practically all metals having solid salts)

In the foregoing reaction schemes, X is an anion having a negative charge m, such as, e.g., halide anion, sulfate anion, carbonate anion, phosphate anion, among others; n is a positive integer; and Me represents a metal atom. R in the foregoing reaction schemes can be chosen from a wide variety of radicals.

Suitable carboxylic acids for use in making metal carboxylates include, for example:

Monocarboxylic Acids:

Monocarboxylic acids where R is hydrogen or unbranched hydrocarbon radical, such as, for example, HCOOH—formic, CH$_3$COOH—acetic, CH$_3$CH$_2$COOH—propionic, CH$_3$CH$_2$CH$_2$COOH(C$_4$H$_8$O$_2$)—butyric, C$_5$H$_{10}$O$_2$—valeric, C$_6$H$_{12}$O$_2$—caproic, C$_7$H$_{14}$—enanthic; further: caprylic, pelargonic, undecanoic, dodecanoic, tridecylic, myristic, pentadecylic, palmitic, margaric, stearic, and nonadecylic acids;

Monocarboxylic acids where R is a branched hydrocarbon radical, such as, for example, (CH$_3$)$_2$CHCOOH—isobutyric, (CH$_3$)$_2$CHCH$_2$COOH—3-methylbutanoic, (CH$_3$)$_3$CCOOH—trimethylacetic, including VERSATIC 10 (trade name) which is a mixture of synthetic, saturated carboxylic acid isomers, derived from a highly-branched C$_{10}$ structure;

Monocarboxylic acids in which R is a branched or unbranched hydrocarbon radical containing one or more double bonds, such as, for example, CH$_2$=CHCOOH—acrylic, CH$_3$CH=CHCOOH—crotonic, CH$_3$(CH$_2$)$_7$CH=CH(CH$_2$)$_7$COOH—oleic, CH$_3$CH=CHCH=CHCOOH—hexa-2,4-dienoic, (CH$_3$)$_2$—HCH$_2$CH$_2$C(CH$_3$)=CHCOOH—3,7-dimethyl-octa-2,6-dienoic, CH$_3$(CH$_2$)$_4$CH=CHCH$_2$CH=CH(CH$_2$)$_7$COOH—linoleic, further: angelic, tiglic, and elaidic acids;

Monocarboxylic acids in which R is a branched or unbranched hydrocarbon radical containing one or more triple bonds, such as, for example, CH≡CCOOH—propiolic, CH$_3$C≡CCOOH—tetrolic, CH$_3$(CH$_2$)$_4$C≡CCOOH—oct-2-ynoic, and stearolic acids;

Monocarboxylic acids in which R is a branched or unbranched hydrocarbon radical containing one or more double bonds and one or more triple bonds;

Monocarboxylic acids in which R is a branched or unbranched hydrocarbon radical containing one or more double bonds and one or more triple bonds and one or more aryl groups;

Monohydroxymonocarboxylic acids in which R is a branched or unbranched hydrocarbon radical that contains one hydroxyl substituent, such as, for example, HOCH$_2$COOH—glycolic, CH$_3$CHOHCOOH—lactic, C$_6$H$_5$CHOHCOOH—amygdalic, and 2-hydroxybutyric acids;

Dihydroxymonocarboxylic acids in which R is a branched or unbranched hydrocarbon radical that contains two hydroxyl substituents, such as, for example, (HO)$_2$CHCOOH—2,2-dihydroxyacetic acid;

Dioxycarboxylic acids, in which R is a branched or unbranched hydrocarbon radical that contains two oxygen atoms each bonded to two adjacent carbon atoms, such as, for example, C$_6$H$_3$(OH)$_2$COOH—dihydroxy benzoic, C$_6$H$_2$(CH$_3$)(OH)$_2$COOH—orsellinic; further: caffeic, and piperic acids;

Aldehyde-carboxylic acids in which R is a branched or unbranched hydrocarbon radical that contains one aldehyde group, such as, for example, CHOCOOH—glyoxalic acid;

Keto-carboxylic acids in which R is a branched or unbranched hydrocarbon radical that contains one ketone group, such as, for example, CH$_3$COCOOH—pyruvic, CH$_3$COCH$_2$COOH—acetoacetic, and CH$_3$COCH$_2$CH$_2$COOH—levulinic acids;

Monoaromatic carboxylic acids, in which R is a branched or unbranched hydrocarbon radical that contains one aryl substituent, such as, for example, C$_6$H$_5$COOH—benzoic, C$_6$H$_5$CH$_2$COOH—phenylacetic, C$_6$H$_5$CH(CH$_3$)COOH—2-phenylpropanoic, C$_6$H$_5$CH=CHCOOH—3-phenylacrylic, and C$_6$H$_5$C≡CCOOH—3-phenyl-propiolic acids;

Multicarboxylic Acids:

Saturated dicarboxylic acids, in which R is a branched or unbranched saturated hydrocarbon radical that contains one carboxylic acid group, such as, for example, HOOC—COOH—oxalic, HOOC—CH$_2$—COOH—malonic, HOOC—(CH$_2$)$_2$—COOH—succinic, HOOC—(CH$_2$)$_3$—COOH—glutaric, HOOC—(CH$_2$)$_4$—COOH—adipic; further: pimelic, suberic, azelaic, and sebacic acids;

Unsaturated dicarboxylic acids, in which R is a branched or unbranched hydrocarbon radical that contains one carboxylic acid group and a carbon-carbon multiple bond, such as, for example, HOOC—CH=CH—COOH—fumaric; further: maleic, citraconic, mesaconic, and itaconic acids;

Polybasic aromatic carboxylic acids, in which R is a branched or unbranched hydrocarbon radical that contains a aryl group and a carboxylic acid group, such as, for example, C$_6$H$_4$(COOH)$_2$—phthalic (isophthalic, terephthalic), and C$_6$H$_3$(COOH)$_3$—benzyl-tri-carboxylic acids;

Polybasic saturated carboxylic acids, in which R is a branched or unbranched hydrocarbon radical that contains a carboxylic acid group, such as, for example, ethylene diamine N,N'-diacetic acid, and ethylene diamine tetraacetic acid (EDTA);

Polybasic Oxyacids:

Polybasic oxyacids, in which R is a branched or unbranched hydrocarbon radical containing a hydroxyl substituent and a carboxylic acid group, such as, for example, HOOC—CHOH—COOH—tartronic, HOOC—CHOH—CH$_2$—COOH—malic, HOOC—C(OH)=CH—COOH—oxaloacetic, HOOC—CHOH—CHOH—COOH—tartaric, and HOOC—CH$_2$—C(OH)COOH—CH$_2$COOH—citric acids.

A metal compound composition, in some embodiments of the present invention, comprises a solution of carboxylic acid salts of one or more metals ("metal carboxylate"). A liquid metal carboxylate composition can comprise a single metal, to form a single metal carboxylate, or a mixture of metals, to form a corresponding mixture of metal carboxylates. In addition, a liquid metal carboxylate composition can contain different carboxylate moieties. In some embodiments, a liquid metal carboxylate composition contains a mixture of metals, as these compositions form mixed oxides having various properties.

Solvent used in the production of liquid metal carboxylate compositions, in some embodiments, comprise an excess of the liquid carboxylic acid which was used to form the metal carboxylate salt. In other embodiments, a solvent comprises another carboxylic acid, or a solution of a carboxylic acid in another solvent, including, but not limited to, organic solvents such as benzene, toluene, chloroform, dichloromethane, or combinations thereof.

Carboxylic acids suitable for use generating liquid metal carboxylate compositions, in some embodiments, are those which: (1) can form a metal carboxylate, where the metal carboxylate is soluble in excess acid or another solvent; and (2) can be vaporized in a temperature range that overlaps with the oxide conversion temperature range.

In some embodiments, a carboxylic acid has a formula R—COOH, where R is alkyl, alkenyl, alkynyl or aryl.

In some embodiments, the monocarboxylic acid comprises one or more carboxylic acids having the formula I below:

$$R^o\text{—}C(R'')(R')\text{—}COOH \qquad (I)$$

wherein:
$R^o$ is selected from H or $C_1$ to $C_{24}$ alkyl groups; and
R' and R" are each independently selected from H and $C_1$ to $C_{24}$ alkyl groups;
wherein the alkyl groups of $R^o$, R', and R" are optionally and independently substituted with one or more substituents, which are alike or different, chosen from hydroxy, alkoxy, amino, and aryl radicals, and halogen atoms.

The term alkyl, as used herein, refers to a saturated straight, branched, or cyclic hydrocarbon, or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl, heptyl, octyl, nonyl, and decyl.

The term alkoxy, as used herein, refers to a saturated straight, branched, or cyclic hydrocarbon, or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl, heptyl, octyl, nonyl, and decyl, in which the hydrocarbon contains a single-bonded oxygen atom that can bond to or is bonded to another atom or molecule.

The terms alkenyl and alkynyl, as used herein, refer to a straight, branched, or cyclic hydrocarbon, including $C_1$ to $C_{24}$, with a double or triple bond, respectively.

Alkyl, alkenyl, alkoxy, and alkynyl radicals are unsubstituted or substituted with one or more alike or different substituents independently chosen from halogen atoms, hydroxy, alkoxy, amino, aryl, and heteroaryl radicals.

Moreover, the term aryl or aromatic, as used herein, refers to a monocyclic or bicyclic hydrocarbon ring molecule having conjugated double bonds about the ring. In some embodiments, the ring molecule has 5- to 12-members, but is not limited thereto. The ring may be unsubstituted or substituted having one or more alike or different independently-chosen substituents, wherein the substituents are chosen from alkyl, alkenyl, alkynyl, alkoxy, hydroxyl, and amino radicals, and halogen atoms. Aryl includes, for example, unsubstituted or substituted phenyl and unsubstituted or substituted naphthyl.

The term heteroaryl as used herein refers to a monocyclic or bicyclic aromatic hydrocarbon ring molecule having a heteroatom chosen from O, N, P, and S as a member of the ring, and the ring is unsubstituted or substituted with one or more alike or different substituents independently chosen from alkyl, alkenyl, alkynyl, hydroxyl, alkoxy, amino, alkylamino, dialkylamino, thiol, alkylthio, =O, =NH, =PH, =S, and halogen atoms. In some embodiments, the ring molecule has 5- to 12-members, but is not limited thereto.

The alpha branched carboxylic acids, in some embodiments, have an average molecular weight ranging from about 130 to 420 g/mol or from about 220 to 270 g/mol. The carboxylic acid may also be a mixture of tertiary and quaternary carboxylic acids of Formula I. VIK acids can be used as well. See U.S. Pat. No. 5,952,769, at col. 6, II. 12-51, which patent is incorporated herein by reference in its entirety.

In some embodiments, one or more metal carboxylates can be synthesized by contacting at least one metal halide with at least one carboxylic acid in the substantial absence of water. In other embodiments, the contacting occurs in the substantial absence of a carboxylic anhydride, yet in specific embodiments at least one carboxylic anhydride is present. In still other embodiments, the contacting occurs in the substantial absence of a catalyst; however, particular embodiments provide at least one catalyst. For example, silicon tetrachloride, aluminum trichloride, titanium tetrachloride, titanium tetrabromide, or a combination of two or more thereof can be mixed into 2-ethylhexanoic acid, glacial acetic acid, or another carboxylic acid or a combination thereof in the substantial absence of water with stirring to produce the corresponding metal carboxylate or combination thereof. Carboxylic anhydrides and/or catalysts can be excluded, or are optionally present. In some embodiments, the carboxylic acid is present in excess. In other embodiments, the carboxylic acid is present in a stoichiometric ratio to the at least one metal halide. Certain embodiments provide the at least one carboxylic acid in a stoichiometric ratio with the at least one metal halide of about 1:1, about 2:1, about 3:1, or about 4:1. The contacting of the at least one metal halide with at least one carboxylic acid can occur under any suitable conditions. For example, the contacting optionally can be accompanied by heating, partial vacuum, and the like.

Either a single carboxylic acid or a mixture of carboxylic acids can be used to form the liquid metal carboxylate. In some embodiments, a mixture of carboxylic acids contains 2-ethylhexanoic acid wherein $R^o$ is H, R" is $C_2H_5$ and R' is $C_4H_9$, in the formula (I) above. The use of a mixture of carboxylates can provide several advantages. In one aspect, the mixture has a broader evaporation temperature range, making it more likely that the evaporation temperature of the acid mixture will overlap the metal carboxylate decomposition temperature, allowing the formation of a metal oxide coating. Moreover, the possibility of using a mixture of carboxylates avoids the need and expense of purifying an individual carboxylic acid.

Other metal compounds can be used to form metal oxides in accordance with the present invention. Such metal compounds can be used alone or in combination, or in combination with one or more metal carboxylates. Metal compounds other than carboxylates and those mentioned elsewhere include metal alkoxides and metal β-diketonates.

Metal alkoxides suitable for use in the present invention include a metal atom and at least one alkoxide radical —$OR^2$ bonded to the metal atom. Such metal alkoxides include those of formula II:

$$M(OR^2)_z \qquad (II)$$

in which M is a metal atom of valence z+;
z is a positive integer, such as, for example, 1, 2, 3, 4, 5, 6, 7, and 8;
$R^2$ can be alike or different and are independently chosen from unsubstituted and substituted alkyl, unsubstituted and substituted alkenyl, unsubstituted and substituted alkynyl, unsubstituted and substituted heteroaryl, and unsubstituted and substituted aryl radicals,
wherein substituted alkyl, alkenyl, alkynyl, heteroaryl, and aryl radicals are substituted with one or more alike or different substituents independently chosen from halogen, hydroxy, alkoxy, amino, heteroaryl, and aryl radicals.
In some embodiments, z is chosen from 2, 3, and 4.

Metal alkoxides are available from Alfa-Aesar and Gelest, Inc., of Morrisville, Pa. Lanthanoid alkoxides such as those of Ce, Nd, Eu, Dy, and Er are sold by Kojundo Chemical Co., Saitama, Japan, as well as alkoxides of Al, Zr, and Hf, among others. See, e.g., http://www.kojundo.co.jp/English/Guide/material/lanthagen.html.

Examples of metal alkoxides useful in embodiments of the present invention include methoxides, ethoxides, propoxides, isopropoxides, and butoxides and isomers thereof. The alkoxide substituents on a given metal atom are the same or different. Thus, for example, metal dimethoxide diethoxide, metal methoxide diisopropoxide t-butoxide, and similar metal alkoxides can be used. Suitable alkoxide substituents also may be chosen from:
1. Aliphatic series alcohols from methyl to dodecyl including branched and isostructured.
2. Aromatic series alcohols: benzyl alcohol—$C_6H_5CH_2OH$; phenyl-ethyl alcohol—$C_8H_{10}O$; phenyl-propyl alcohol—$C_6H_{12}O$, and so on.

Metal alkoxides useful in the present invention can be made according to many suitable methods. One method includes converting the metal halide to the metal alkoxide in the presence of the alcohol and its corresponding base. For example:

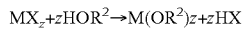

$$MX_z + zHOR^2 \rightarrow M(OR^2)_z + zHX$$

in which M, $R^2$, and z are as defined above for formula II, and X is a halide anion.

Metal β-diketonates suitable for use in the present invention contain a metal atom and a β-diketone of formula III as a ligand:

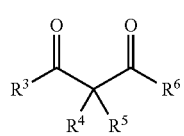

(III)

in which
$R^3$, $R^4$, $R^5$, and $R^6$ are alike or different, and are independently chosen from hydrogen, unsubstituted and substituted alkyl, unsubstituted and substituted alkoxy, unsubstituted and substituted alkenyl, unsubstituted and substituted alkynyl, unsubstituted and substituted heteroaryl, unsubstituted and substituted aryl, carboxylic acid groups, ester groups having unsubstituted and substituted alkyl, and combinations thereof, wherein substituted alkyl, alkoxy, alkenyl, alkynyl, heteroaryl, and aryl radicals are substituted with one or more alike or different substituents independently chosen from halogen atoms, hydroxy, alkoxy, amino, heteroaryl, and aryl radicals.

It is understood that the β-diketone of formula III may assume different isomeric and electronic configurations before and while chelated to the metal atom. For example, the free β-diketone may exhibit enolate isomerism. Also, the β-diketone may not retain strict carbon-oxygen double bonds when the molecule is bound to the metal atom.

Examples of β-diketones useful in embodiments of the present invention include acetylacetone, trifluoroacetylacetone, hexafluoroacetylacetone, 2,2,6,6-tetramethyl-3,5-heptanedione, 6,6,7,7,8,8,8-heptafluoro-2,2-dimethyl-3,5-octanedione, ethyl acetoacetate, 2-methoxyethyl acetoacetate, benzoyltrifluoroacetone, pivaloyltrifluoroacetone, benzoyl-pyruvic acid, and methyl-2,4-dioxo-4-phenylbutanoate.

Other ligands are possible on the metal β-diketonates useful in the present invention, such as, for example, alkoxides such as —$OR^2$ as defined above, and dienyl radicals such as, for example, 1,5-cyclooctadiene and norbornadiene.

Metal β-diketonates useful in the present invention can be made according to any suitable method. β-diketones are well known as chelating agents for metals, facilitating synthesis of the diketonate from readily available metal salts.

Metal β-diketonates are available from Alfa-Aesar and Gelest, Inc. Also, Strem Chemicals, Inc. of Newburyport, Mass., sells a wide variety of metal β-diketonates on the internet at http://www.strem.com/code/template.ghc?direct=cvdindex.

In some embodiments, a metal compound composition contains one metal compound as its major component and one or more additional metal compounds which may function as stabilizing additives. Stabilizing additives, in some embodiments, comprise trivalent metal compounds. Trivalent metal compounds include, but are not limited to, chromium, iron, manganese and nickel carboxylates. A metal compound composition, in some embodiments, comprises both cerium and chromium carboxylates.

In some embodiments, the amount of metal forming the major component of the metal compound composition ranges from about 65 weight percent to about 97 weight percent or from about 80 weight percent to about 87 weight percent of the total metal in the compound composition. In other embodiments, the amount of metal forming the major component of the metal compound composition ranges from about 90 weight percent to about 97 weight percent of the total metal present in the compound composition. In a further embodiment, the amount of metal forming the major component of the metal compound composition is less than about 65 weight percent or greater than about 97 weight percent of the total metal present in the compound composition.

In some embodiments, metal compounds operable to function as stabilizing additives are present in amounts such that the total amount of the metal in metal compounds which are the stabilizing additives is at least 3% by weight of the total metal in the liquid metal compound composition.

The amount of metal in a liquid metal compound composition, according to some embodiments, ranges from about 0.2 to about 150 grams of metal per kilogram of liquid metal compound composition. In other embodiments, the amount of metal in a liquid metal compound composition ranges from about 1 to about 5 grams, from about 5 to about 10 grams, from about 10 to about 25 grams, from about 25 to about 50 grams, or from about 5 to about 50 grams of metal per kilogram of liquid metal compound composition. In a further embodiment, a liquid metal compound composition comprises from about 10 to about 40 grams of metal per kg of composition. In one embodiment, a metal amount is less than about 0.2 grams of metal per kilogram of liquid metal compound or greater than 150 grams of metal per kilogram of liquid metal compound.

Liquid metal compound compositions, in some embodiments of solid oxide cell production methods, further comprise one or more catalytic materials, such as one or more interfacial catalysts mentioned above. Catalytic materials, in certain embodiments, comprise transition metals including, but not limited to, platinum, palladium, rhodium, nickel, cerium, gold, silver, zinc, lead, ruthenium, rhenium, or mixtures thereof. Catalytic materials, in some embodiments, are present in liquid metal compound compositions in an amount ranging from about 0.5 weight percent to about 10 weight percent of the composition. In further embodiments, one or more catalytic materials are present in an amount of less than about 0.5 weight percent of the composition. In still further embodiments, one or more catalytic materials are present in an amount of greater than about 10 weight percent of the composition. In certain embodiments, the catalytic material is present in the liquid metal compound composition in the form of a metal compound. In certain other embodiments, the catalytic material is present in the form of a metal, such as, for example, a metal nanopowder.

In other embodiments, a liquid metal compound composition further comprises nanoparticles operable to alter the pore structure and porosity of the metal oxide resulting from the conversion of the liquid metal compound composition. Nanoparticles, in some embodiments, comprise metal oxide nanoparticles. Nanoparticles, in some embodiments, are present in liquid metal compound compositions in an amount ranging from about 0.5 percent by volume to about 30 percent by volume of the liquid metal compound composition. In another embodiment, nanoparticles are present in the liquid metal compound composition in an amount ranging from about 5 percent by volume to about 15 percent by volume of the liquid metal compound composition.

In addition to liquids, metal compound compositions, in some embodiments of the present invention, comprise solid metal compound compositions, vapor metal compound compositions, or combinations thereof. In one embodiment, a solid metal compound composition comprises one or more metal compound powders. In another embodiment, a vapor metal compound composition comprises a gas phase metal compound operable to condense on a substrate prior to conversion to a metal oxide. In some embodiments, the substrate is cooled to enhance condensation of the vapor phase metal compound composition. In one embodiment, for example, a substrate such as a glass substrate is placed in a vacuum chamber, and the chamber is evacuated. Vapor of one or more metal compounds, such as cerium (IV) 2-hexanoate, enters the vacuum chamber and deposits on the steel substrate. Subsequent to deposition, the metal compound is exposed to conditions operable to convert the metal compound to a metal oxide. In a further embodiment, a metal compound composition comprises gels chosen from suitable gels including, but not limited to, sol-gels, hydrogels, and combinations thereof.

Electrolyte can be formed on the substantially-planar substrate in any suitable manner. In some cases, that involves applying a metal compound to a surface of the substantially-planar substrate, and exposing the metal compound to an environment that will convert at least some of the metal compound to a metal oxide. In one embodiment, substantially-planar substrates such as suitable glass squares or rectangles are dipped in a liquid metal compound composition comprising zirconium metal compounds and yttrium metal compounds. Then the substrates are slowly drawn from the liquid, leaving a uniform liquid coat on both sides of the substrates. The substrates are placed in an oven that is heated to 450° C. and allowed to gradually cool to room temperature, thereby forming an yttria-stabilized zirconia electrolyte on both surfaces. Optionally, the substrates are dipped in another metal compound composition, this one containing platinum compounds. Upon gradual extraction and heating in an oven set to 450° C., the substrates now have a first interface between an yttria-stabilized zirconia material and the substrate, and a second interface between a platinum oxide material and the yttria-stabilized zirconia material. The substrates are allowed to cool to room temperature.

The cooled substrates are then assembled into a rig, with each electrolyte-coated substrate separated from each other by placing spacer elements such as glass capillary tubes between the substrates. In some cases, if the assembled substrates with the glass capillary tubes are heated in an oven set to 650° C., the electrolyte and the tubes will bind with some degree of permanence. If the glass capillary tubes are arranged parallel for the length of the substrates, passages are defined by the substrates and the tubes.

Then, a plurality of first electrodes disposed on the substrates in ionic communication with the electrolyte are formed in the passages. The first electrodes can be formed in any suitable manner. Similarly, a plurality of second electrodes disposed on the substrates in ionic communication with the electrolyte and electrically isolated from the plurality of first electrodes are formed in the passages. In some embodiments, the first electrodes and the second electrodes are formed at the same time, and it is later decided which will be first electrodes and which will be second electrodes. One method to form electrodes is to place the assembled substrates containing electrolyte and bonded capillary tubes in a vacuum vessel with the substantially-planar substrates being perpendicular to the horizontal, exposing the passages between the substrates. Then an electrode composition, such as one containing a second metal compound and conductive particles in a solvent such as chloroform, is poured over the substrates and allowed to flow into the passages. The vacuum vessel is sealed and a vacuum is drawn on the vessel. The electrode composition boils, and it is believed that the boiling action mixes the electrode composition, evenly distributing the ingredients and penetrating the electrolyte's features. Accordingly, some embodiments provide the applying an electrode composition to the substrates is performed under reduced pressure.

Upon removal from the vacuum vessel, the electrode composition dries quickly on the electrolyte of the assembled substrates. The assembled substrates are placed in an oven and heated to a temperature suitable to convert the second metal compound into metal oxide, such as 450° C., and allowed to cool. Optionally, the electrode composition is poured into the passages from the opposite side, and vacuuming and heating are repeated for a second coat of electrodes in the passages. The assembled substrates now coated with electrolyte and having electrodes filling each passage is ready for operation as a cell. It remains to be chosen which passages will be first passages with first electrodes, and which passages will be second passages with second electrodes. Any suitable choice can be made. In one embodiment, any two adjacent passages having contiguous electrolyte are chosen one to be a first passage and the other to be a second passage.

Any suitable method for converting a metal compound can be used. In some cases, exposing a metal compound to an environment that will convert at least some of the metal compound to a metal oxide comprises heating the metal compound. Converting a metal compound, according to some embodiments of the present invention, comprises exposing the metal compound to an environment operable to convert the metal compound to a metal oxide. Environments operable to convert metal compounds to metal oxides, in some embodiments, provide conditions sufficient to vaporize and/or decompose the compound moieties and precipitate metal oxide formation. In one embodiment, an environment operable to convert metal compounds to metal oxides comprises a heated environment. A metal salt of a carboxylic acid, for example, can be exposed to an environment heated to a temperature operable to convert the carboxylic acid and induce formation of the metal oxide. In some embodiments, the environment is heated to a temperature greater than about 200° C. In other embodiments, the environment is heated to a temperature greater than about 400° C. In certain embodiments, the environment is heated to a temperature up to about 425° C. or up to about 450° C. In additional embodiments, the environment is heated to a temperature ranging from about 400° C. to about 650° C. In a further embodiment, the environment is heated to a temperature ranging from about 400° C. to about 550° C.

The rate at which the environment is heated to effect the conversion of the at least one metal compound to the at least one metal oxide is not limited. In some embodiments, the heating rate is less than about 7° C./minute. In other embodiments, the heating rate is equal to about 7° C./minute. In still other embodiments, the heating rate is greater than about 7° C./minute. The heating rate, according to certain iterations of the present invention, is equal to the heating rate of the oven in which the conversion takes place. Particular embodiments provide a heating rate that is as fast as the conditions and equipment allow.

In some embodiments, the metal oxide penetrates into the substrate to a depth ranging from about 0.5 nm to about 100 nm or from about 20 nm to about 80 nm. In other embodiments, the metal oxide penetrates into the substrate to a depth ranging from about 30 nm to about 60 nm or from about 40 nm to about 50 nm. Converting the metal compound on the substrate to a metal oxide, in some embodiments, produces a transition layer comprising metal oxide and substrate material, in some embodiments. In other embodiments, the metal oxide does not penetrate into the substrate and an abrupt interface exists between the metal oxide and the substrate.

Moreover, exposing metal compound compositions to environments operable to convert the compositions to metal oxides, as provided herein, eliminates or reduces the need for sintering to produce metal oxides. By eliminating sintering, solid oxide cell production methods of the present invention gain several advantages. One advantage is that the lower temperatures of some methods of the present invention do not induce grain growth or other degradative processes in various components of the solid oxide cell during production. Another advantage is that the compound compositions permit tailoring of individual metal oxide layers in the construction of electrolytes and electrodes. Methods of the present invention, for example, permit one metal oxide layer of an electrolyte or electrode to have completely different compositional and/or physical parameters in comparison to an adjacent metal oxide layer, in some embodiments. Such control over the construction of electrolytes and electrodes of solid oxide cells is extremely difficult and, in many cases, not possible with present sintering techniques. In other embodiments, for example, one material can be prepared with conventional techniques such as sintering or epitaxial growth, while a metal oxide can be formed on that material without the need for sintering.

The conversion environment, for various embodiments of the present invention, can be any suitable environment, and the conversion can be precipitated by any suitable means. In some embodiments of the present invention, the substrate is heated; in others, the atmosphere about the metal compound composition is heated; in still others, the metal compound composition is heated. In further embodiments, a substrate having a metal compound composition deposited thereon can be heated in an oven, or exposed to heated gas. The conversion environment may also be created using induction heating through means familiar to those skilled in the art of induction heating. Alternatively, the conversion environment may be provided using a laser applied to the surface area for sufficient time to allow at least some of the metal compounds to convert to metal oxides. In other applications, the conversion environment may be created using an infrared light source which can reach sufficient temperatures to convert at least some of the metal compounds to metal oxides. Some embodiments may employ a microwave emission device to cause at least some of the metal compound to convert. Other embodiments provide a plasma to heat the metal compound. In the case of induction heating, microwave heating, lasers, plasmas, and other heating methods that can produce the necessary heat levels in a short time, for example, within seconds, 1 minute, 10 minutes, 20 minutes, 30 minutes, 40 minutes, or one hour.

In some cases, after an yttria-stabilized zirconia material is formed on a substrate, thereby forming an electrolyte, a platinum oxide material can be formed on the yttria-stabilized zirconia material. Thus, in certain embodiments, before applying an electrode composition, a platinum metal compound is applied to the electrolyte, and the platinum metal compound is exposed to an environment that will convert at least some of the platinum metal compound to a platinum oxide.

Certain cases provide electrodes comprising one or more conductive particles. Any suitable conductive particles can be used. In some instances, the conductive particle comprises silver-coated nickel flakes, silver-coated nickel spheres, silver-coated nanoparticles of another metal such as iron, nickel-iron alloys such as Invar and Kovar, silver nanoparticles, copper nanoparticles, gold nanoparticles, or a combination of two or more thereof. The conductive particles can be introduced to the electrodes in any suitable manner. In some instances, the conductive particles are mixed into an electrode composition that includes one or more metal compounds. Any suitable metal compounds can be included, such as, for example, a zirconium metal compound, an yttrium metal compound, a platinum metal compound, and combinations thereof. The conductive particles can be present in the electrode composition in any suitable amount, such as, for example, at least 10 g metal/kg electrode composition, at least 20 g particles/kg electrode composition, at least 30 g particles/kg electrode composition, at least 40 g particles/kg electrode composition, at least 100 g particles/kg electrode composition, or at least 200 g particles/kg electrode composition.

Some embodiments of the present invention include electrodes. Any suitable electrode material can be used. Electrodes of the present invention, in some embodiments, comprise silicon carbide doped with titanium. Certain embodiments comprise platinum, platinum oxide, YSZ, silver, and combinations of two or more thereof. In other embodiments, an electrode comprises $La_{1-x}Sr_xMnO_3$ [lanthanum strontium doped manganite (LSM)]. In another embodiment, an electrode comprises one or more porous steel alloys. In one embodiment, a porous steel alloy comprises steel alloy 52. In some embodiments, a porous steel alloy suitable for use as an electrode comprises steel alloy 316, stainless steel alloy 430, Crofer 22 APU® (Thyssen Krupp), E-Brite® (Alleghany Ludlum), HASTELLOY® C-276, INCONEL® 600, or HASTELLOY® X, each of which is commercially available from Mott Corporation of Farmington, Conn. Yet additional embodiments provide an electrode comprising nickel such as, for example, Nickel Alloy 200. Certain embodiments employ an electrode comprising porous graphite, optionally with one or more catalytic materials. In a further embodiment, an electrode comprises any metal or alloy known to one of skill in the art operable to serve as an electrode. Some embodiments of the present invention provide electrodes comprising a metal, a metal carbide, or a combination thereof. Certain additional embodiments provide an electrode comprising titanium silicate carbide. In some of those embodiments, the electrode material may have electrical, structural, and mechanical properties that are better than those of ceramic electrodes.

Electrodes in certain embodiments of the present invention comprise platinum oxide, platinum, YSZ, silver particles, nickel particles, silver-coated nickel flakes, silver-coated nickel particles, silver colloid, or a combination of two or more thereof. Such a composition can be made by depositing on the electrolyte, optionally into an exposure made in the layered electrolyte, a composition comprising a Pt(II) salt, yttrium carboxylates, zirconium carboxylates, silver particles, nickel particles, silver-coated nickel flakes, silver-coated nickel particles, silver colloid, or a combination thereof. Other optional ingredients include, but are not limited to, soda glass powder and other metal colloid. Particle sizes for the various particles and powders is not limited and can be on the micrometer scale in one embodiment. One Pt(II) salt is Pt (II) 2,4-pentanedionate available from Alfa Aesar. Optionally, platinum oxide can be reduced to form metallic platinum by any suitable method, such as, for example, baking in an $Ar/H_2$ atmosphere at 600° C. for 15 minutes.

Electrodes, according to further embodiments of the present invention, are porous. In some embodiments, an electrode has a porosity ranging from about 5% to about 40%. In another embodiment, an electrode has a porosity ranging from about 10% to about 30% or from about 15% to about 25%. In a further embodiment, an electrode has a porosity greater than about 40%. An electrode, in some embodiments, has a porosity ranging from about 40% to about 80%. In one embodiment, an electrode has a porosity greater than about 80%.

An electrode, in one embodiment, is an anode. An electrode, in another embodiment, is a cathode. In some embodiments, a metal oxide coating of an electrode can protect the electrode substrate from corrosion and/or degradation. In additional embodiments of the methods of the present invention, the electrolyte on the substrate forms an interface adapted to allow ionic conductivity along the interface. Once the electrodes have been formed on the substrates, and optionally on the electrolytes, further embodiments relate to adding an ion-conducting species to at least some of the electrodes.

Some embodiments relate to methods of operating a solid oxide cell that comprises a first electrode and a second electrode, electrically isolated from each other and in ionic communication with an electrolyte, the method comprising: contacting at least one of the electrodes with an ion-conducting species. Any suitable substrate, metal oxide electrolyte, electrodes, operating temperature, and fuel, can be used. Any suitable ion-conducting species can be used as well. In some cases, the ion-conducting species is chosen from water, salt water, an ionic liquid, and combinations of two or more thereof. In other cases, the ion-conducting species comprises tetrafluoroborate.

Still further embodiments relate to methods of operating a solid oxide cell, which cell comprises an electrolyte comprising at least one interface between an yttria-stabilized zirconia material and a glass material, a first electrode and a second electrode electrically isolated from each other and in ionic communication with the electrolyte, the method comprising:

connecting the first electrode in electrical communication to an external circuit; connecting the second electrode in electrical communication to an external circuit;

providing an oxygen-containing gas to the first electrode;
providing a fuel-containing gas to the second electrode; and
heating or maintaining the cell to a temperature at which the cell provides electrical energy to the external circuit.

Certain embodiments provide an oxygen-containing fluid flowing over an electrode such as a cathode. Such a fluid can be in any suitable form, such as gas or liquid. The oxygen-containing fluid is not limited by composition, and can be air, dry air, pure oxygen, or oxygen mixed with another gas such as nitrogen, argon, helium, neon, or combinations thereof. The oxygen-containing fluid can contact the electrode at any suitable pressure, such as, for example, atmospheric pressure, less than atmospheric pressure, or greater than atmospheric pressure. Certain embodiments provide the oxygen-containing fluid to the cathode at a pressure greater than about 1 atm, greater than about 5 atm, or greater than about 10 atm. In some cases, the oxygen-containing fluid is preheated. In other cases, the oxygen-containing fluid is precooled.

Other embodiments provide a fuel-containing fluid. Such a fluid is not limited by form, temperature, pressure, or composition. In some cases, the fuel-containing fluid is hydrogen gas, or contains molecular hydrogen. Hydrogen can be in the presence of an inert carrier gas, such as, for example, nitrogen, argon, helium, neon, or combinations thereof. The fuel-containing fluid can contact the electrode at any suitable pressure, such as, for example, atmospheric pressure, less than atmospheric pressure, or greater than atmospheric pressure. Certain embodiments provide the fuel-containing fluid to the anode at a pressure greater than about 1 atm, greater than about 5 atm, or greater than about 10 atm. In some cases, the fuel-containing fluid is preheated. In other cases, the fuel-containing fluid is precooled. In still other cases, the fuel-containing fluid is the product of the reformation of hydrocarbons.

Any suitable operating temperature can be used. The operating temperature of the cell can be no greater than 250° C., no greater than 200° C., no greater than 150° C., no greater than 100° C., no greater than 50° C., or no greater than 30° C. Some embodiments provide cell operating temperatures at greater than 30° C., greater than 50° C., greater than 100° C., greater than 150° C., greater than 200° C., greater than 250° C., greater than 400° C., greater than 500° C., greater than 750° C., or greater than 900° C. Still other embodiments provide cell operating temperatures at less than 30° C., less than 20° C., less than 10° C., or less than 0° C.

Certain instances provide that to maintain a desired temperature for the cell, the cell actually has to be cooled.

Cooling a cell can be accomplished by any suitable method. The environment around the cell can be cooled, such as by air conditioning; cooling fluid can be piped around the supporting rig where present; one or both of the oxygen-containing gas and the fuel-containing gas can be cooled before contacting the electrodes; or a combination of suitable methods can cool the cell.

Heat generated by the operation of a cell, a module, or a module assembly can be dealt with in any suitable fashion. In some embodiments, the flow of oxygen-containing fluid, fuel-containing fluid, or both is increased or decreased to aid in maintaining the desired operating temperature of the cell, module, or module assembly. For example, the fuel-containing fluid can be hydrogen gas flowing past the anodes in the module assembly. In the vicinity of the anodes, the hydrogen will pick up water vapor developed as the module assembly operated in fuel cell mode. The steam-laden hydrogen gas is then passed to a liquid nitrogen-cooled condenser apparatus, whereby water condenses out of the hydrogen gas. The dry hydrogen is returned to the anodes, and in this manner transports thermal energy away from the cells. In other embodiments, one or more heat sinks are in thermal communication with the cell, module, or module assembly. A heat sink is any thermal energy-absorbing or conducting material that allows heat generated in a cell to move away from the cell. For example, a metal in thermal communication with a cell can dissipate heat from the cell, such as by heat transfer along the metal. In another example, the rig can have a cooling fluid circulating in thermal communication with the cell supported by the rig. The cooling fluid is then passed to a heat exchanger, for example, thereby dissipating the heat generated during operation.

Minaturization

Applicants have unexpectedly found on certain dimensional scales, a solid oxide cell of the present invention can be reduced in size without sacrificing cell performance. For example, reducing the dimensions of a cell from 40 mm×20 mm to 20 mm×10 mm cuts the area of the cell by a factor of four. However, the electrical power output of the cell operated in fuel cell mode does not change. Without wishing to be bound by theory, it is believed that various factors causing performance loss at a larger scale are reduced at the smaller scale, thereby making up for the expected loss in cell performance at the smaller scale. Chief among those factors is the relative proximity of the anode to the cathode at larger scale, it is believed. The closer the anode to the cathode, the better the cell performs, it is further believed. This reduction in size without loss of performance has been observed at the centimeter and millimeter scale, and is expected to continue into the micron scale. This surprising result affords an opportunity to reduce cell size and material cost, while increasing cell longevity and performance. It also urges the development of systems employing larger numbers of smaller cells, rather than a fewer number of large, smaller cells. Accordingly, Applicants have developed what are referred to herein as modules, which can be thought of as a convenient collection of cells, and a module assembly, which is a convenient collection of modules.

Thus, some embodiments of the present invention provide planar layered solid oxide electrolyte wherein the cell occupies an area smaller than those conventionally known. In some cases, the area of an electrolyte, including the area "covered" by electrodes, is less than about 1000 $mm^2$, less than about 500 $mm^2$, less than about 200 $mm^2$, less than about 100 $mm^2$, less than about 10 $mm^2$, or less than about 1 $mm^2$.

Electrolyzers

Some embodiments of the present invention provide solid oxide electrolyzer cells or a component thereof comprising a metal oxide. In certain embodiments, the electrolyzer cell or component thereof is substantially identical in manufacture and composition as the other solid oxide cells and components described herein.

In some of those embodiments of the present invention where the same cell can function as an electrolyzer cell and alternately as a fuel cell simply by reversing the flow of electrons, the cathode of the electrolyzer corresponds to the fuel electrode of the fuel cell; and the anode of the electrolyzer corresponds to the air electrode of the fuel cell. Those of ordinary skill in the art recognize that oxidation occurs at the anode, and reduction occurs at the cathode, so the name of a given electrode may differ depending on whether the cell is operating as an electrolyzer or as a fuel cell.

In other embodiments, electrons flow in the same direction, regardless of whether the cell is electrolyzing or producing electricity. This can be accomplished, for example, by supplying oxygen anions to a given electrode in electrolysis mode, and alternately supplying hydrogen to the same electrode in fuel cell mode. Such an electrode will function as the oxidizing anode in either mode.

Accordingly, some embodiments of the present invention provide a solid oxide electrolyzer cell, comprising a first electrode, a second electrode, and a metal oxide electrolyte interposed between the first electrode and the second electrode. Further embodiments relate to contacting at least one electrode of a solid oxide electrolyzer cell with at least one ion-conducting species.

The present invention also provides, in some embodiments, a method for making a product, comprising:

providing a solid oxide cell comprising a first electrode, a second electrode, and an electrolyte interposed between the first electrode and the second electrode, wherein the electrolyte comprises an interface between an yttria-stabilized zirconia material and a glass material;

contacting the first electrode with a reactant; and supplying electrical energy to the first electrode and the second electrode thereby causing the reactant to undergo electrochemical reaction to yield the product.

The skilled electrochemist will appreciate that a complete circuit is necessary for electrical energy to cause electrochemical reaction. For example, at least one ion may traverse the metal oxide electrolyte to complete the electrical circuit at the second electrode. Moreover, a second product may be formed at the second electrode due to electrochemical reaction. Therefore, some embodiments further provide for contacting the second electrode with a second reactant, thereby causing the second reactant to undergo electrochemical reaction to yield a second product. Contacting an electrode and supplying electrical energy can occur in any suitable order. In a continuous process, electrical energy supply is maintained while additional reactant(s) enter the cell and product(s) are removed.

Any suitable reactant can be supplied to an electrode for electrochemical reaction. Suitable reactants include, but are not limited to, water such as, for example, pure water, fresh water, rain water, ground water, salt water, purified water, deionized water, water containing a ionic substance, brine, acidified water, basified water, hot water, superheated water, steam, carbon dioxide, carbon monoxide, hydrogen, nitrous oxides, sulfur oxides, ammonia, metal salts, molten metal salts, and combinations thereof. Ionic substances include those substances that release an ion when placed in contact with water, and include, but are not limited to, salts, acids, bases, and buffers. Reactants, and for that matter, products, can be in any suitable form, including solid, liquid, gas, and combinations thereof. Solid reactants and/or solid products lend themselves to batch processes, although suitable methods for continuously removing a solid product from a cell can be employed. Fluid reactants and products can appear in either batch or continuous processes. Optionally, heat energy is applied to the reactant, the product, at least one electrode, the metal oxide, the cell, or a combination thereof.

Some embodiments provide a sacrificial electrode. A sacrificial electrode itself reacts in the electrolysis process, and is thereby consumed or rendered unreactive as the reaction proceeds. For example, a zinc electrode can be consumed in a suitable solid oxide cell reaction, yielding $Zn^{2+}$ and two electrons per atom of zinc consumed. In another example, an electrode can become coated and thereby rendered unreactive by solid product forming on its surface. The unreactive electrode can be removed from the cell, and the product extracted from the electrode, or the product can be used on the electrode in another process. The electrode then can be regenerated, recycled, or discarded. Alternatively, a sacrificial electrode can be made to gradually insert into a cell at a rate consistent with the rate at which the electrode is consumed.

A reactant undergoing electrochemical reaction can be oxidized and/or reduced, and chemical bonds may form and/or break. For example, when water undergoes electrolysis, hydrogen-oxygen bonds break, $H^+$ is reduced to $H^0$, $O^{2-}$ is oxidized to $O^0$, and $H_2$ and $O_2$ form, in some circumstances. Hydrogen peroxide and other species may form in other circumstances. The skilled artisan will appreciate that many electrode half reactions can be substituted so that any variety of anions, cations, and other species may result from electrochemical reaction.

In one embodiment, water containing NaCl can be electrolyzed to form hydrogen gas and NaOH at the cathode, and chlorine gas at the anode, in the so-called chlor-alkali process:

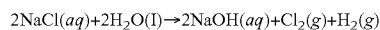

$$2NaCl(aq)+2H_2O(l) \rightarrow 2NaOH(aq)+Cl_2(g)+H_2(g)$$

A solid oxide cell arranged to carry out that reaction, in some embodiments, provides water containing a high concentration of NaCl (for example, saturated) to a first electrode that will act as an anode, and provides water to a second electrode that will act as a cathode. The cell also provides liquid effluent collection to remove the depleted NaCl solution from the anode, and NaOH-containing water from the cathode. The cell further provides gas effluent collection to remove chlorine gas from the anode and hydrogen gas from the cathode. Optionally, the hydrogen and chlorine can be subject to electrochemical reaction to release the electrochemical energy stored by the foregoing electrolysis, or they can be used for other industrial processes, such as the synthesis of sodium hypochlorite.

The present invention also provides methods for storing electrochemical energy. In some embodiments, a reactant is supplied to an electrode of a solid oxide cell, the reactant undergoes one or more electrochemical reactions and yields a fuel, thereby storing electrochemical energy. The electrochemical reaction may also yield other products, such as cations, anions, and other species, some of which may form at a second electrode of the solid oxide cell that completes an electrical circuit. A first electrode and a second electrode are separated by a metal oxide electrolyte in the solid oxide cell. The fuel can be subjected to energy conversion processes such as reverse electrochemical reaction in a fuel cell or battery, combustion, and the like to release the stored electrochemical energy.

In one embodiment, electrochemical energy is stored by providing a reactant to a cathode; reducing the reactant at the cathode to release an anion and a fuel; storing the fuel; transporting the anion through a metal oxide electrolyte to anode; and oxidizing the anion. Optionally, the oxidized anion is stored as well, separately from the stored fuel. Thus, in one embodiment, water in a suitable form is supplied to a cathode, at which it is reduced to hydrogen ($H_2$) and oxygen anion ($O^{2-}$); the hydrogen is collected and stored, while the oxygen anion diffuses through a solid metal oxide electrolyte to an anode where the oxygen anion is oxidized to oxygen ($O_2$). Optionally, in the foregoing non-limiting example, the oxygen is collected and stored as well.

When desired, the stored hydrogen can be fed to any suitable fuel cell, including but not limited to the cell that produced the hydrogen, and the hydrogen can be oxidized to release the stored electrochemical energy. Any suitable gas can be fed to the air electrode of the fuel cell, such as, for example, the optionally-stored oxygen, other oxygen, other oxygen-containing gas such as air, and combinations thereof. Alternatively, the stored hydrogen can be combusted with oxygen to propel a rocket, drive a piston, rotate a turbine, and the like. In other embodiments, the stored hydrogen can be used in other industrial processes, such as petroleum cracking.

Some embodiments involve those reactants that yield the high energy materials commonly found in primary (nonrechargeable) and secondary (rechargeable) batteries. For secondary battery materials, the low-energy (discharge) state materials may be produced, since secondary batteries can be charged before first use. Such materials include, but are not limited to, $MnO_2$, $Mn_2O_3$, $NH_4Cl$, $HNO_3$, $LiCl$, $Li$, $Zn$, $ZnO$, $ZnCl_2$, $ZnSO_4$, $HgO$, $Hg$, $NiOOH$, $Ni(OH)_2$, $Cd$, $Cd(OH)_2$, $Cu$, $CuSO_4$, $Pb$, $PbO_2$, $H_2SO_4$, and $PbSO_4$.

At least some embodiments of fuel cells described above can be used to provide electrolyzer cell embodiments of the present invention. While fuel cell embodiments optionally employ one or more of fuel supply, air or oxidizer supply, interconnects, and electrical energy harvesting means (e.g., wires forming a circuit between the fuel and air electrodes' interconnects), electrolyzer cell embodiments optionally employ one or more of reactant supply, fuel collection, interconnects, and electrical energy supply. Optionally, electrolyzer cell embodiments also provide collection means for other products in addition to fuel. The reactant supply provides any suitable reactant for electrolysis. Fuel collection, in some embodiments, involves collecting hydrogen for storage and later use. Storage vessels, metal hydride technology, and other means for storing hydrogen are known in the art. Fuel collection, in other embodiments, involves collection of, for example, carbon-coated electrodes for later oxidation. Alternatively, carbon can be formed into fluid hydrocarbon for easy storage and later combustion or reformation. Hydrocarbon formation requires a supply of hydrogen molecules, atoms, or ions in a suitable form to combine with carbon at the cathode, in some embodiments. Other product collection involves, in some embodiments, the collection of oxygen for storage and later use.

In still other embodiments, an electrolyzer cell is capable of performing other electrolysis tasks, such as electroplating. In such embodiments, a metal oxide functions as a solid electrolyte shuttling a ion to complete an electrical circuit.

In some embodiments, the electrodes of the electrolyzer cell are adapted for the particular electrochemistry expected to occur at the given electrode. For example, the electrode can comprise one or more catalytic materials to facilitate the electrochemical reaction.

Sensors

Some embodiments of the present invention provide solid oxide sensors or components thereof. Like the fuel cells and electrolyzer cells described herein, sensors of the present invention comprise a metal oxide electrolyte. In some embodiments, at least one ion passes through that metal oxide electrolyte during cell operation. In other embodiments, the solid oxide cells useful as sensors or components thereof are substantially identical to the solid oxide cells and components described above. The metal oxide electrolyte of sensors in certain embodiments has been made according to a process comprising:
applying a metal compound to a substrate, and
converting at least some of the metal compound to a metal oxide, thereby forming an electrolyte,
wherein the electrolyte has an ionic conductivity greater than the bulk ionic conductivity of the metal oxide.

Further embodiments relate to contacting at least one electrode of a solid oxide sensor with at least one ion-conducting species.

Sensors according to various embodiments of the present invention can be used to detect any suitable analyte or analytes. Oxygen sensors, useful as lambda sensors in automotive exhaust systems, or as oxygen partial pressure detectors in rebreather systems, represent some applications for embodiments. Other sensors, such as gas sensors including but not limited to CO, $CO_2$, $H_2$, $NO_x$, and $SO_x$; ion sensors including but not limited to pH meters, $K^+$, and $Na^+$; biosensors including but not limited to glucose sensors and other enzyme electrodes; electrochemical breathalyzers; and electronic noses; represent other applications for embodiments of the present invention. Many such sensors function at least in part due to the diffusion of an ion through an electrolyte, which electrolyte comprises a metal oxide.

Accordingly, additional embodiments provide a method for detecting an analyte, comprising:
providing a sensor for the analyte, wherein the a sensor comprises a metal oxide made by a process comprising:
applying a metal compound to a substrate, and
converting at least some of the metal compound to the metal oxide, wherein the metal oxide electrolyte has an ionic conductivity greater than the bulk ionic conductivity of the metal oxide; and
passing an ion through the metal oxide to detect the analyte. Passing an ion through a metal oxide can include any suitable transport mechanism, such as, for example, diffusion. In addition, movement along metal oxide crystal grain boundaries represents another transport mechanism, in some embodiments. Detecting an analyte can indicate obtaining any useful information about the analyte, such as, for example, determining its mere presence, concentration, partial pressure, oxidation state, or combinations thereof. And, sensors of the present invention can be designed for any suitable environment, such as solid, semisolid (e.g., soil), liquid, gas, plasma, and combinations thereof. Also, such sensors can be designed for any suitable operating temperature, ranging from the very cold to the very hot. Some solid oxide cells useful as sensors according to the present invention have an operating temperature of below about −195° C., below about −182° C., below about −77° C., from about −78° C. to about 0° C., from about 0° C. to about 100° C., from about 100° C. to about 400° C., from about 400° C. to about 600° C., from about 600° C. to about 900° C., from about 900° C. to about 1200° C., or above about 1200° C. Other embodiments useful as sensors have operating temperatures below about 0° C., above about 0° C., above about 100° C., or above about 500° C.

A few embodiments of the present invention provide solid oxide cells, useful as sensors, that enjoy one or more advantages over conventional sensors. In some embodiments, the metal oxide has a certain thickness, thinner than conventional sensors. In other embodiments, the solid oxide cell operates at a lower temperature, compared to conventional sensors. Still other embodiments provide smaller sensors. Even other embodiments provide sensors made from less-expensive materials. Additional embodiments have better-matched coefficients of thermal expansion between two or more materials in the cell. Still other embodiments provide one or more concentration gradients, one or more porosity gradients, or combinations thereof.

Further embodiments of the present invention provide a sensor comprising at least two electrodes separated by a layered metal oxide that functions as an electrolyte. In some of those embodiments, the voltage difference between the at least two electrodes corresponds to the concentration of the analyte being detected at one of the electrodes. A first electrode functions as a reference electrode, and is exposed to a reference environment. Suitable reference environments include, but are not limited to, air, vacuum, standard solutions, and environments of known or controlled composition. In some embodiments, the reference environment is formed by arranging one or more materials that substantially isolate the reference electrode from the environment being measured. The second electrode is exposed to the environment being measured. Optionally, the second electrode comprises one or more catalytic materials. In operation, the first and second electrodes are placed in electrical communication with one or more devices that can measure, for example, the voltage difference, the current, the resistance, or combinations thereof, between the two electrodes. Such devices are known in the art. Optionally, heat or cooling can be supplied to one or both electrodes, the electrolyte, or combinations thereof. Heat or cooling can come from any suitable source, such as, for example, one or more electrical resistance heaters, chemical reaction, thermal fluid in thermal communication with the sensor, the measured environment, and combinations thereof.

In some embodiments, a reference voltage is supplied to the electrodes, and the current needed to maintain the reference voltage corresponds to the concentration of the analyte being measured. For example, U.S. Pat. No. 7,235,171, describes two-electrode hydrogen sensors comprising barium-cerium oxide electrolyte. The '171 patent also indicates that various other metal oxides also function as electrolytes in hydrogen sensors, including selenium cerium oxides, selenium cerium yttrium oxides, and calcium zirconium oxides, which conduct protons, and oxygen anion conductors. The '171 patent is incorporated herein by reference in its entirety.

In other embodiments, a gas permeable porous platinum measuring electrode is exposed to a measured environment that contains a partial pressure of oxygen. A metal oxide, such as, for example, yttria-stabilized zirconia, separates the measuring electrode from a gas permeable porous platinum reference electrode that is exposed to air. The voltage difference, current, or both between the electrodes can be measured and correlated to the difference of partial pressure of oxygen between the measured environment and air. In some embodiments, the measured environment is an exhaust stream from the combustion of hydrocarbons.

In still other embodiments, at least two pairs of electrodes appear, wherein a layered metal oxide electrolyte separates the electrodes in each pair. One of the two pairs functions as a reference cell, while the other of the two pairs functions as a measuring cell, in some embodiments. Further embodiments provide, in a first pair of electrodes, a reference electrode exposed to a reference environment and a Nernst electrode exposed to the measured environment. A metal oxide that functions as an electrolyte is situated between the reference electrode and the Nernst electrode. In a second pair of electrodes, an inner pump electrode is separated from an outer pump electrode, with a metal oxide functioning as an electrolyte situated between the inner and outer pump electrodes. The inner pump electrode and the Nernst electrode are exposed to the environment to be measured optionally through a diffusion barrier. In operation, an external reference voltage is applied across the pump electrodes. The current needed to maintain the reference voltage across the pump electrodes provides a measure of the analyte concentration in the measured environment. For a conventional broadband lambda sensor containing such a pair of electrodes, see U.S. Pat. No. 7,083,710 B2, which is incorporated herein by reference in its entirety. Optionally, a sensor of the present invention is adapted to electrically communicate with control circuitry that smooths operation of the sensor before the sensor has achieved standard operating conditions, such as temperature. See, for example, U.S. Pat. No. 7,177,099 B2, which is also incorporated herein by reference in its entirety.

Thus, certain embodiments of the present invention provide so-called narrow band sensors such as lambda sensors that fluctuate between lean and rich indications. Other embodiments provide broadband sensors such as lambda sensors that indicate the partial pressure of oxygen, and thereby the degree of leanness or richness of an air-fuel mixture.

Some embodiments provide more than two electrodes. For example, a sensor according to the present invention may contain a plurality of measuring electrodes. For another example, a sensor may comprise a plurality of reference electrodes. In another example, a sensor may comprise, or be adapted to electrically communicate with, a standard electrode or other device providing information useful to the operation of the sensor.

DETAILED DESCRIPTION OF THE DRAWINGS

Further embodiments of the present invention can be described by reference to the accompanying drawings.

FIG. 1 shows, in one embodiment of the invention, a schematic of a cell according to one embodiment of the present invention. The cell in this case is a fuel cell, having a cathode (110) and an anode (120), both in ionic communication with an yttria-stabilized zirconia material (150) acting as electrolyte. The yttria-stabilized zirconia material forms an interface (130) with a glass substrate (140). Also depicted is ionic conduction (160) into the electrolyte from the cathode (110), ionic conduction (170) along the interface (130), ionic conduction (175) through the bulk of the electrolyte, and ionic conduction (165) from the electrolyte into the anode (120).

Figure 2:
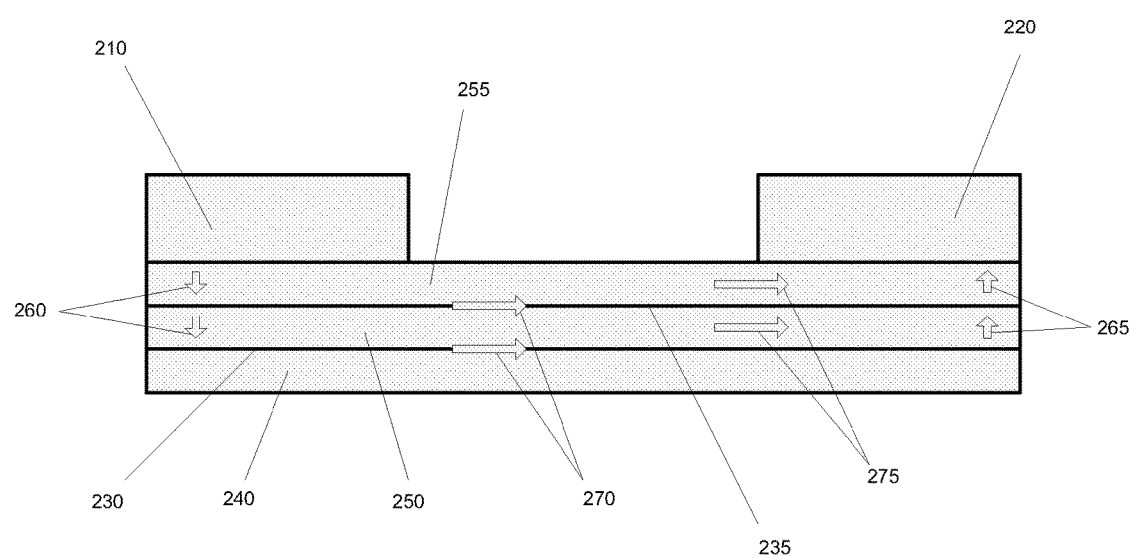
FIG. 2 depicts schematically another embodiment of the invention comprising a cathode (210), an anode (220), and electrolyte comprising a first interface (230) between a yttria-stabilized zirconia material (250) and a glass material (240), and a second interface (235) between a platinum oxide material (255) and the yttria-stabilized zirconia material (250).

FIG. 2 shows, schematically, another embodiment operating as a fuel cell with a cathode (210) and an anode (220) in ionic communication with an electrolyte having an yttria-stabilized zirconia material (250) that forms a first interface (230) with a glass substrate (240), and a second interface (235) with a platinum oxide material (255). As oxygen reacts at the cathode (210) to form $O^{2-}$ anions, those anions pass into the electrolyte via bulk ionic conduction (260). Those anions proceed along the first interface (230) and/or the second interface (235), and/or via bulk ionic conduction (275). Near the anode (220), the anions reach a region of the electrolyte adapted for bulk ionic conductivity (265) as the anions flow from the electrolyte to the anode (220).

Figure 3:
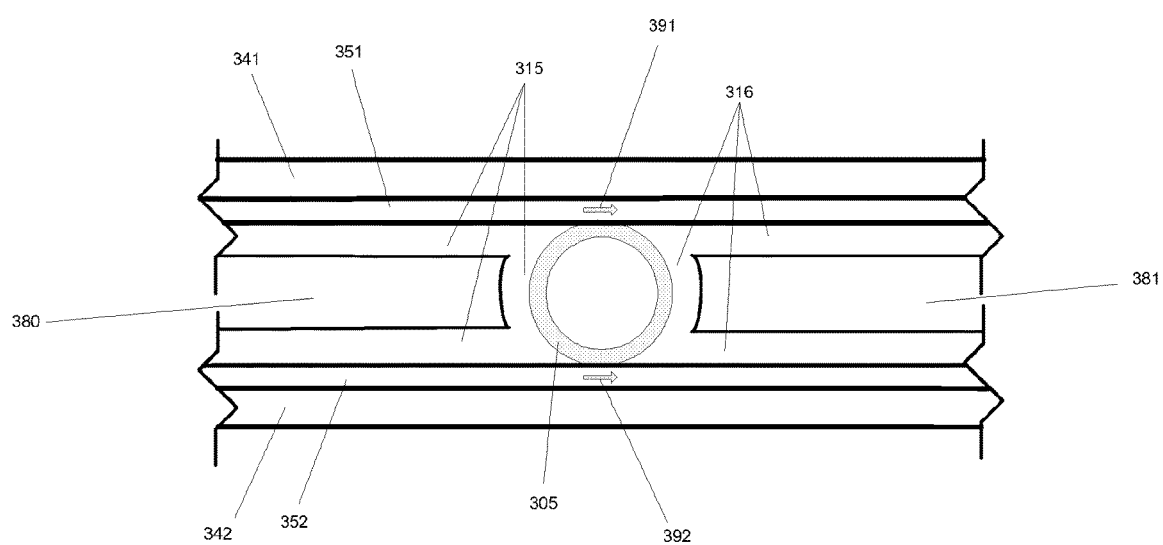
FIG. 3 depicts schematically a further embodiment in partial view, in which a glass capillary tube (305) viewed end on is sandwiched between two glass substrates (341, 342) that contain electrolyte (351, 352) and a first electrode (315) and a second electrode (316).

FIG. 3 depicts, schematically, a partial view of an embodiment of the present invention. In this embodiment, a cell having two glass substrates (341, 342), has been constructed. On the glass substrates (341, 342), an electrolyte (351, 352) has been formed. For this illustration, the exact identity of the electrolyte (351, 352) is not limited. Upon forming the electrolyte (351, 352), the glass substrates (341, 342) were separated by a spacer element that is a glass capillary tube (305). Heated to a suitable temperature, such as about 650 C, for example, the electrolyte (351, 352) bonded with the glass capillary tube (305). The substrates (341, 342) with electrolyte (351, 352) and the glass capillary tube (305) define a first passage (380) and a second passage (381). Into the passages (380, 381) was added an electrode composition, which yielded a first electrode (315) and a second electrode (316). If air or other oxygen-containing fluid is passed into first passage (380), and hydrogen gas or other fuel-containing fluid is passed into second passage (381), then the first electrode (315) will operate as a cathode, and the second electrode (316) will operate as an anode. Arrows (391, 392) depict ionic conduction through a very small region of electrolyte (351, 352) that separates the first electrode (315) and the second electrode (316). It is believed that the very small distance between the electrodes (315, 316) adds greatly to the performance of the cells employing glass capillary tubes (305) in this manner. It should be noted that FIG. 3 also shows two interfaces between a domain of electrolyte (e.g., 351) and glass materials: The first interface is with the glass substrate (341), and the second interface is with the glass capillary tube (305).

Figure 4:
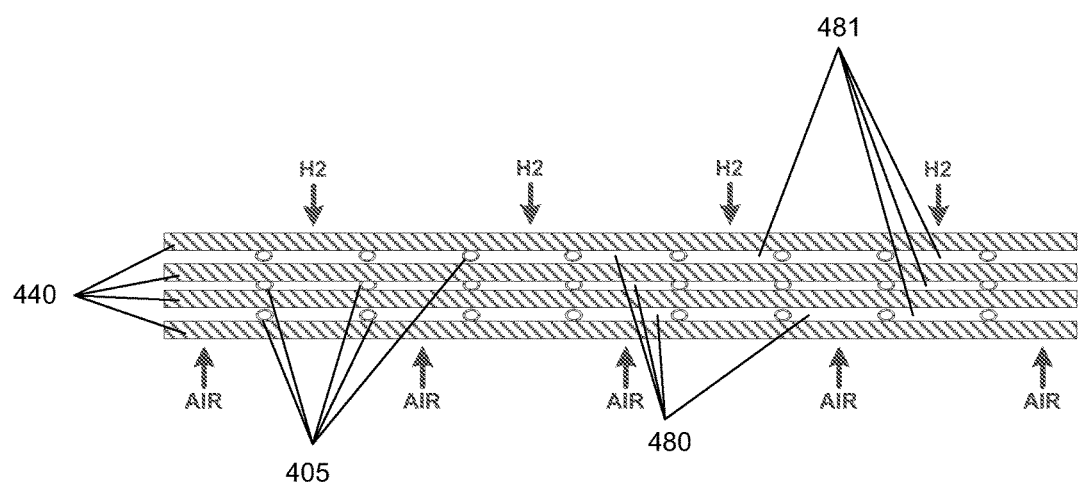
FIG. 4 depicts schematically a side view of a further embodiment in which glass capillary tubes (405) act as spacer elements between multiple glass substrates (440), which define first passages (480) and second passages (481).

FIG. 4 shows another embodiment of the present invention, in which the partial view of FIG. 3 could appear. Viewed from the side, substantially-planar substrates (440) made of glass are separated by numerous glass capillary tubes (405) (not all glass capillary tubes are labeled, for clarity). The substrates (440) further contain electrolyte (not shown) and electrodes (not shown) (see FIG. 3). The substrates (440) and glass capillary tubes (405) define first passages (480) (not all first passages are labeled, for clarity) and second passages (481) (not all second passages are labeled, for clarity). A fuel-containing fluid or gas input manifold (not shown) can be affixed to the second passages (481) to supply hydrogen gas ("H2" in FIG. 4). An oxygen-containing fluid or gas input manifold (not shown) can be affixed to the first passages (480) to supply air ("AIR" in FIG. 4), or, optionally, the first passages can be left open to ambient air.

Figure 5:
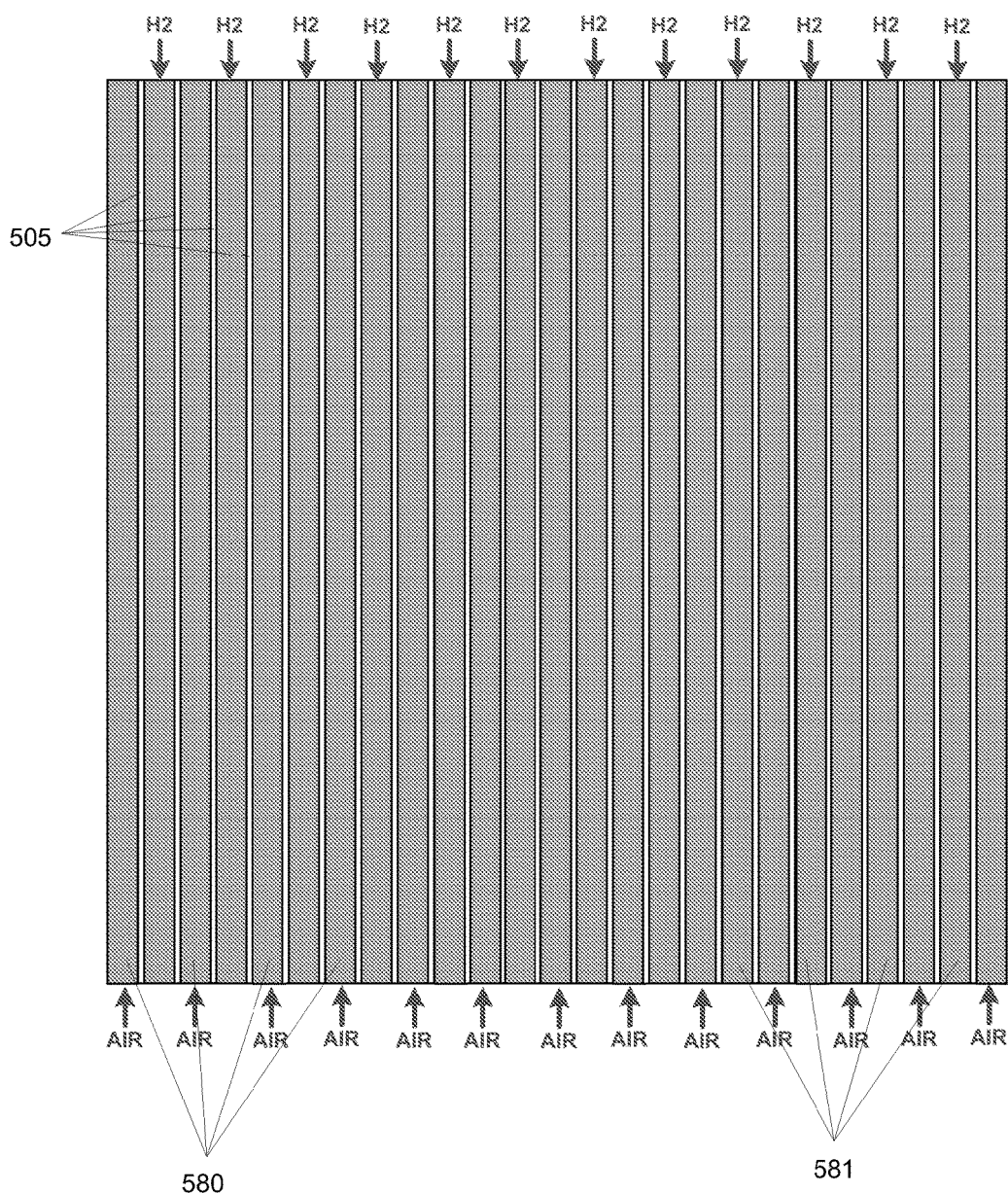
FIG. 5 depicts another embodiment in a top view showing glass capillary tubes (505) define first passages (580) and second passages (581) in a solid oxide cell.

FIG. 5 shows another embodiment, similar to the embodiment shown in FIG. 4, except FIG. 5 is seen from the top, and contains more passages. Glass capillary tubes (505) arranged in parallel between substantially-planar substrates (not shown) define first passages (580) and second passages (581). When the cell is configured to operate as a solid oxide fuel cell, an oxygen-containing fluid (e.g., "AIR"), can be provided to the first passages (580), while a fuel-containing fluid (e.g., "H2") can be provided to the second passages (581).

Figure 6:
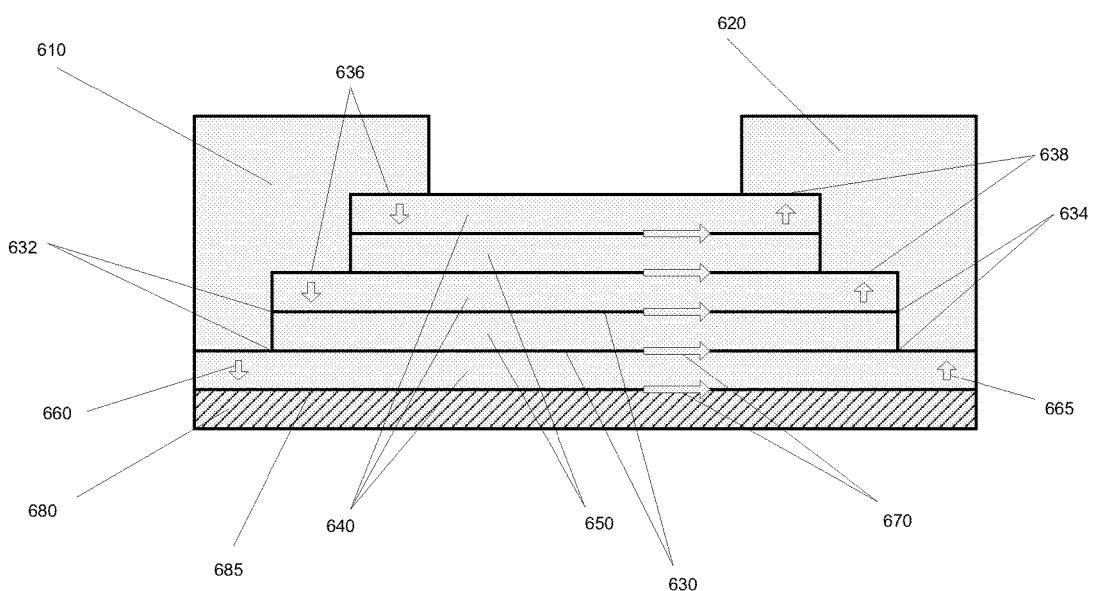
FIG. 6 shows another embodiment wherein underlying layers of yttria-stabilized zirconia (640) are exposed to the cathode (610) and the anode (620). In this embodiment, another metal oxide, strontium titanate (650), also appears.

FIG. 6 shows another embodiment wherein underlying layers of yttria-stabilized zirconia (640) are exposed to the cathode (610) and the anode (620) in a solid oxide cell operated as a fuel cell. This embodiment has an electrolyte comprising alternating layers of yttria-stabilized zirconia (640) and strontium titanate (650) having an interface (630) between each layer. Also shown is an interface (685)

between yttria-stabilized zirconia (640) and a glass substrate (680). The regions (632) where the cathode (610) contacts the interfaces (630) is relatively small, and similarly, the regions (634) where the anode (620) contacts the interfaces (630) also is relatively small. Accordingly, this embodiment takes advantage of the relatively broad cathode-electrolyte contact regions (636) where the cathode (610) contacts the several layers of yttria-stabilized zirconia (640), and the relatively broad anode-electrolyte contact region (638) where the anode (620) contacts the several layers of yttria-stabilized zirconia (640). In the cathode-electrolyte contact regions (636), oxygen ions (not shown) undergo bulk ionic conduction (arrows pointing down, labeled 660) through the yttria-stabilized zirconia (640) to reach the interfaces (630). Along the interfaces (630), the oxygen ions undergo interfacial ionic conduction (horizontal arrows, labeled 670). In the anode-electrolyte contact regions (638), oxygen ions experience bulk ionic conduction (665) toward the anode (620). In the regions labeled (632) and (634), it is also possible that oxygen ions enter and leave the electrolyte via interfacial ionic conductivity (670) without experiencing bulk ionic conductivity (660, 665).

The exposure of underlying layers of yttria-stabilized zirconia can be accomplished according to any suitable method. For example, all six layers of electrolyte (640, 650) can be formed, and then selectively etched, before applying or forming the cathode (610) and anode (620) thereon. Or, initial layers of the electrolyte (640, 650) can be formed, and masks can be used to prevent the formation of electrolyte (640, 650) that completely covers the initial layers. Then the mask is removed, exposing the initial layers of the electrolyte (640, 650) to the cathode (610) and anode (620) formed thereon. For greater visual clarity, each and every one of items 630, 632, 634, 636, 638, 660, 665, and 670 have not been labeled.

The embodiment shown in FIG. 6 enjoys at least three unexpected advantages. First, oxygen ions enter and leave the yttria-stabilized zirconia across broad regions (636, 638). Second, the oxygen ions diffuse through relatively thin, single layers of metal oxide electrolyte (640) to reach the interfaces (630) or the anode (620). As explained elsewhere, a single layer of yttria-stabilized zirconia can be as thin as 2 nm. Third, oxygen ions undergo rapid diffusion (670) along the interfaces (630), and this embodiment employs multiple interfaces (630) for a greater ionic flux. Multiple interfaces means a greater current density is possible, compared to, for example, an electrolyte having but a single interface, or an electrolyte that effectively employs only a single interface due to the unexpected barrier effect of an electrolyte material exhibiting poor bulk ionic conductivity.

Figure 7:
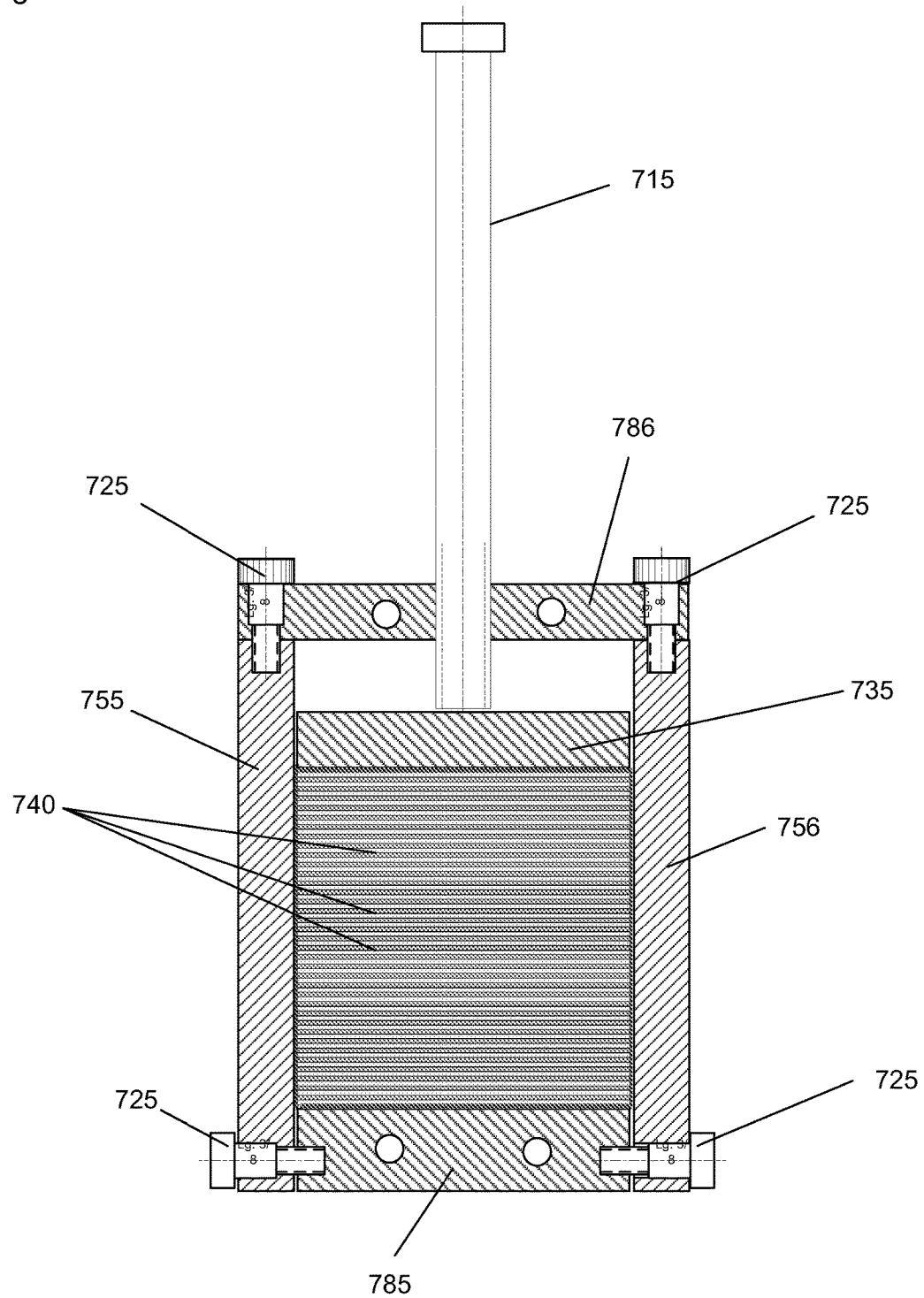
FIG. 7 shows an embodiment of a rig for holding a plurality of substantially-planar substrates (740) for manufacturing electrolyte and/or electrodes on the substrates, and a screw (715) to contact a pressure plate (735) to compress the substantially-planar substrates (740).

FIG. 7 shows a side view of an embodiment of a rig for holding a plurality of substantially-planar substrates (740) for manufacturing electrolyte and/or electrodes on the substrates, and a screw (715) to contact a pressure plate (735) to compress the substantially-planar substrates (740). The screw (715) can be replaced with a plunger, weight, spring-loaded device, or other mechanism for compressing the substrates (740). This embodiment of the rig contains a base (785), side walls (755, 756), and a cover (786), held together by bolts (725) or other suitable fasteners. When the screw (715) is rotated, screw threads (not shown) in the cover (786) cause the screw (715) to increase pressure against the pressure plate (735), which in turn compresses the substrates (740). This is particularly useful when assembling the cell, so that heating the cell causes the substrates (740) having electrolyte (not shown) to bond with spacer elements (not shown), in some embodiments of the present invention. The material of the rig and its components can be any suitable material. Steel, aluminum, plastic, and combinations thereof can be used in certain embodiments, with consideration being given to processing and operating temperatures and conditions.

Figure 8:
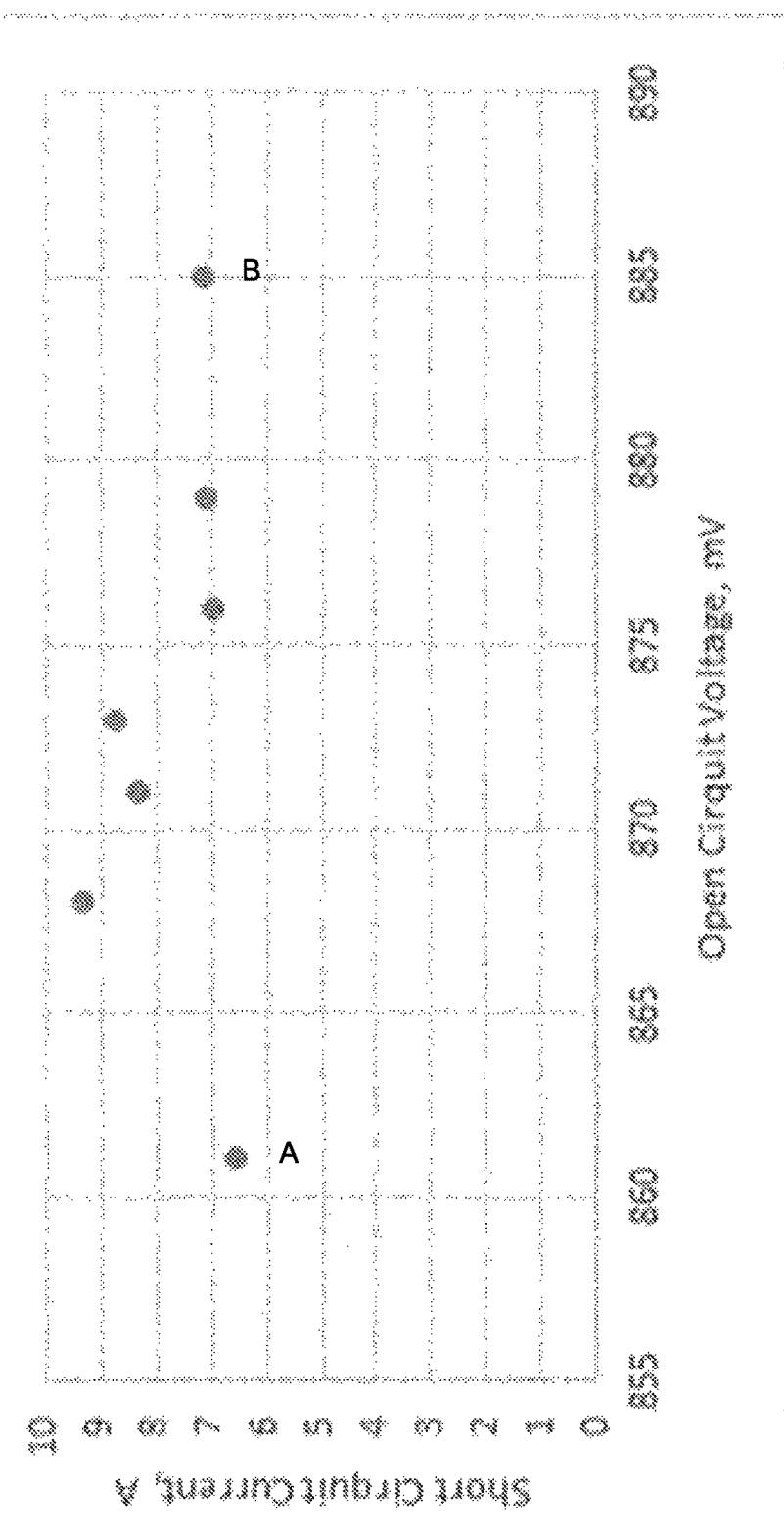
FIG. 8 shows cell performance upon spraying the first electrodes of a solid oxide fuel cell according to some embodiments of the present invention with salt water. Point "A" represents cell performance immediately upon contact with salt water, and point "B," the final data point, represents cell performance less than five minutes later.

FIG. 8 finds greater description in connection with Example 6.

Figure 9:
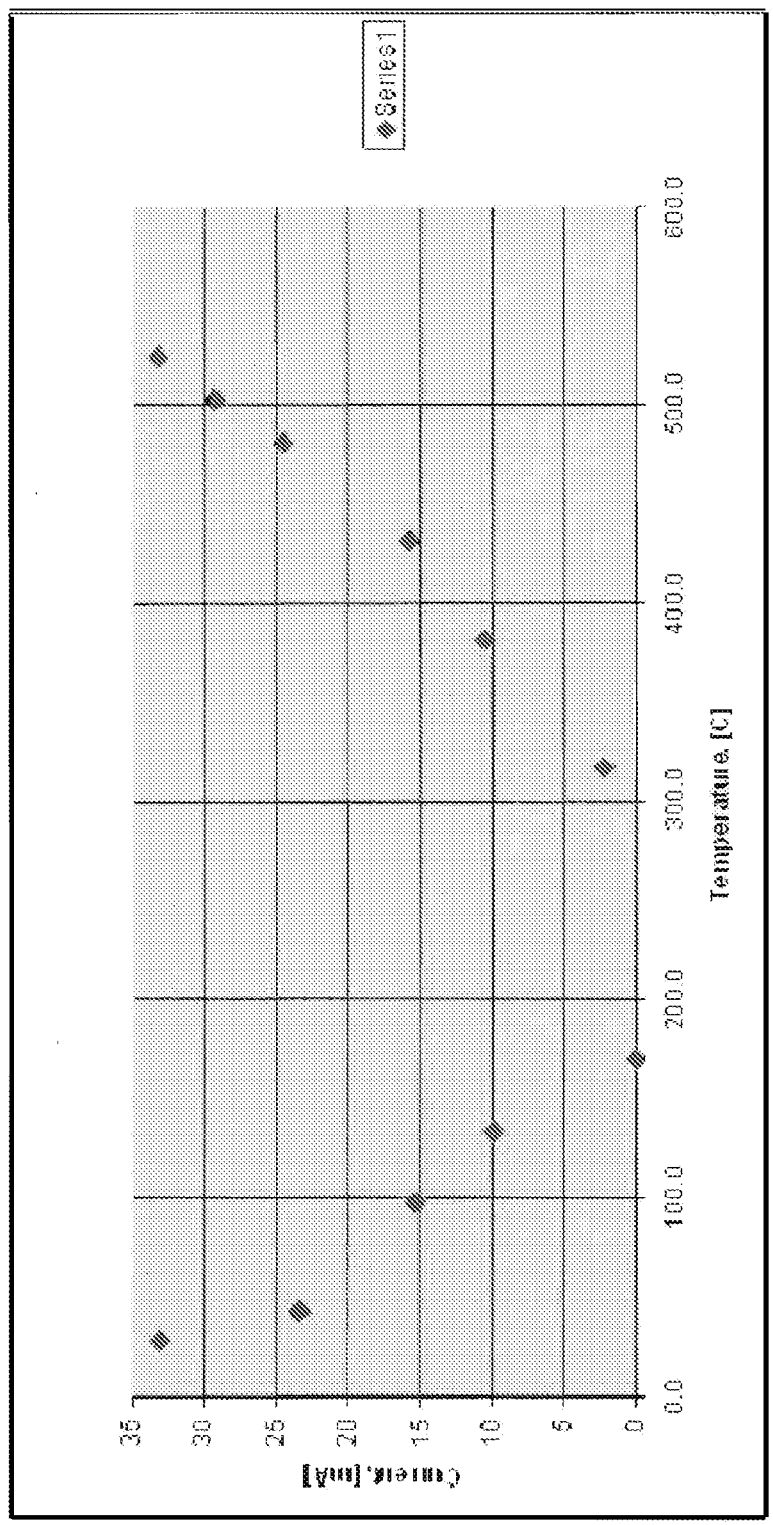
FIG. 9 shows cell performance upon spraying the first electrodes of a solid oxide fuel cell according to some embodiments of the present invention with water. The drop-off in current is believed to be related to the evaporation of water.

FIG. 9 finds greater description in connection with Example 7.

EXAMPLES

The following examples are presented to illustrate the claimed invention but are not to be deemed limitative thereof. Unless otherwise specified, all parts are by weight and all temperatures are in degrees Centigrade. The equipment, materials, volumes, weights, temperatures, sources of materials, manufacturers of equipment, and other parameters are offered to illustrate, but not to limit, the invention. All such parameters can be modified within the scope of the claimed invention.

Example 1—Electrolyte on Glass Substrates

Forty glass microscope slides measuring 1"×3" (Ted Pella, Inc.) were obtained. Each slide was dipped into a composition containing yttrium carboxylates and zirconium carboxylates (2-ethylhexanoates) having a metal concentration of about 1 g/kg, and 15% atomic percent yttrium, withdrawn, heated to 420 to 450° C. in air and allowed to cool, thereby forming a single layer of yttria-stabilized zirconia ("YSZ") on both sides of the glass. Then, the slides were dipped in a composition containing platinum (II) 2,4-pentanedionate in chloroform (Alfa Aesar), having 1 g Pt/kg composition diluted with 2-ethylhexanoic acid, withdrawn, heated to 420 to 450° C., and allowed to cool. The glass slides now had a layer of platinum oxide over a layer of yttria-stabilized zirconia on both planar sides of the glass.

Example 2—Assembling Substrates with Spacer Elements

The electrolyte-coated substrates prepared in Example 1 were stacked together, each slide separated from the one below by two parallel strips of ceramic paper (McMaster) measuring 3" long by 2 mm wide and about 0.5 mm thick. The ceramic paper spacer elements were saturated with high temperature pipe thread sealant (McMaster). Thus, the substrates and the ceramic paper spacer elements formed three passages, two side passages ("first passages") and a central passage ("second passage"). The assembled substrates were compressed together in a rig similar to the one depicted in FIG. 7, heated in an oven set to 200° C. for one hour, and allowed to cool, whereupon it was observed that the electrolyte and the ceramic paper had bonded with the sealant.

Example 3—Forming Electrodes

The assembled substrates with electrolyte were placed in a vacuum vessel with the substrates and ceramic paper spacer elements perpendicular to the horizontal, thereby exposing the passages defined by the substrates and the ceramic paper. An electrode composition containing platinum (II) 2,4-pentanedionate in chloroform (Alfa Aesar) (12 g Pt/kg, about 8% by weight of final electrode composition), yttrium carboxylates and zirconium caboxylates (30 g metal/kg, 15% atomic percent yttrium, about 8% by weight of final electrode composition), nickel flakes coated with silver (45% by weight of final electrode composition), nickel spheres coated with silver (30% by weight of final electrode composition), colloidal silver (Ted Pella) (about 8% by weight of final electrode composition), was poured over assembled substrates into the passages. The vacuum vessel was closed and a vacuum was drawn until the electrode composition began to boil. The assembly was removed and heated to 450° C., and cooled. The electrode composition was poured into the passages from the opposite end of the passages, a vacuum drawn, and the assembly was heated and cooled again. The process was repeated so that three coatings of electrodes were formed in the passages. Thereby electrodes were added to the electrolyte. It was estimated that the electrodes were separated from each other by about 2 mm of electrolyte on either side of the ceramic paper spacer elements.

Example 4—Adding Ion-Conducting Species

The assembled substrates with electrolyte and electrodes were sprayed with salt water (10% by weight NaCl aqueous solution) from a spray bottle. Three conditions were tested: before spraying, immediately after spraying, and again once the salt water had dried.

Example 5—Cell Operation

Silver wires (Ted Pella Inc.) were connected to the electrodes with a conductive silver paste (Ted Pella, Inc.), and the cell was ready for testing. A manifold to supply hydrogen to the central passages defined by the glass capillary tubes was attached to the cell, and an exhaust manifold to collect hydrogen and water was also attached. Hydrogen gas was supplied through the input manifold at a rate of about 1 L/min., and the passages on either side of the cell were left open to air. Condensation of water vapor in the hydrogen exhaust manifold was observed. At a temperature of 27° C., the following performance was also observed:

TABLE 2

Performance of a Solid Oxide Fuel Cell at 27° C.

| Ionic Species | Voc | Isc | V across 100 Ω | I across 100 Ω |
|---|---|---|---|---|
| None | | (microamps) | | |
| Salt Water | 0.8-0.9 V | 9.5 A | 0.775 V | 0.73 A |
| Dried NaCl | 0.7 V | 7 A | | |

Voc = open circuit voltage and Isc = short circuit current

Example 6—Behavior Versus Time

The cell of Examples 1-5 was sprayed with salt water, and the performance of the cell at 27° C. versus time was recorded. In FIG. 8, that performance is reported. Point "A" represents cell performance immediately after the configured cell was sprayed with salt water, and point "B" represents the final data point taken several minutes later. As can be seen in FIG. 8, the short circuit current spikes upon exposure to an ion-conducting species, salt water, and then it levels off. The open circuit voltage continues to climb over the several minutes immediately following contacting the cathodes with salt water.

Example 7—Behavior Versus Temperature: Water as Ion-Conducting Species

A cell similar to the cell of Examples 1-5 was placed in a laboratory oven, and operated at increasing temperature. This cell employed only eleven microscope slides, however, and the ion-conducting species was water. Short circuit current output was measured against increasing temperature. The results appear in FIG. 9. Approximately 34 mA of short circuit current were observed at 27° C. As the temperature increased from room temperature, the current fell off, reaching zero by about 180° C. It is believed that the water contacting the cathodes evaporated, causing the decline and termination of low temperature operation. Current appeared again as the temperature increased above 300° C. 34 mA of current were achieved at approximately 525° C.

EMBODIMENTS

Embodiment 1

An electrolyte for a solid oxide cell, comprising:
at least one interface between an yttria-stabilized zirconia material and a glass material.

Embodiment 2

The electrolyte of embodiment 1, further comprising a platinum oxide material proximal to the yttria-stabilized zirconia material.

Embodiment 3

The electrolyte of any one of embodiments 1-2, wherein the interface is adapted to allow ionic conductivity along the interface.

Embodiment 4

The electrolyte of any one of embodiments 1-3, wherein the electrolyte further comprises:
at least one region adapted to allow ionic conductivity through bulk electrolyte material.

Embodiment 5

The electrolyte of any one of embodiments 1-4, wherein the at least one region is proximal to at least one electrode.

Embodiment 6

The electrolyte of any one of embodiments 1-5, comprising:
a first region adapted to allow ionic conductivity through bulk electrolyte material, wherein the first region is proximal to a first electrode;
a second region adapted to allow ionic conductivity through bulk electrolyte material, wherein the second region is proximal to a second electrode;
wherein the first region is separated from the second region by the at least one interface.

Embodiment 7

The electrolyte of any one of embodiments 1-6, further comprising one or more interfacial catalysts.

Embodiment 8

The electrolyte of any one of embodiments 1-7, wherein the one or more interfacial catalysts are chosen from Li, Ti, Cr, Mn, Fe, Co, Ni, Sr, Sn, Ce, Sm, Gd, Na, K, Cl, and combinations of two or more thereof.

Embodiment 9

The electrolyte of any one of embodiments 1-8, wherein the one or more interfacial catalysts are present in the form of metal oxides, metal nanopowders, or a combination thereof.

Embodiment 10

The electrolyte of any one of embodiments 1-9, comprising:
a first interface between an yttria-stabilized zirconia material and a glass material, and
a second interface between a platinum oxide material and the yttria-stabilized zirconia material.

Embodiment 11

A solid oxide cell comprising:
an electrolyte comprising an interface between an yttria-stabilized zirconia material and a glass material adapted to allow ionic conductivity along the interface;
a first electrode in ionic communication with the interface of the electrolyte; and
a second electrode in ionic communication with the interface of the electrolyte;
wherein the first electrode and second electrode are electrically isolated from each other and are in ionic communication with each other via the interface.

Embodiment 12

A solid oxide cell comprising:
an electrolyte comprising a first interface between an yttria-stabilized zirconia material and a glass material, and a second interface between a platinum oxide material and the yttria-stabilized zirconia material;
a first electrode in ionic communication with the electrolyte; and
a second electrode in ionic communication with the electrolyte;
wherein the first electrode and second electrode are electrically isolated from each other and are in ionic communication with each other via the electrolyte.

Embodiment 13

The solid oxide cell of any one of embodiments 11-12, further comprising an ion-conducting species in contact with the first electrode, the second electrode, or both.

Embodiment 14

The solid oxide cell of any one of embodiments 11-13, wherein the ion-conducting species is chosen from water, salt water, an ionic liquid, inorganic salt, and combinations of two or more thereof.

Embodiment 15

The solid oxide cell of any one of embodiments 11-14, wherein the ion-conducting species comprises tetrafluoroborate, potassium permanganate, NaCl, KCl, or a combination of two or more thereof.

Embodiment 16

The solid oxide cell of any one of embodiments 11-15, comprising:
a plurality of substantially-planar substrates separated by a plurality of spacer elements; each substrate having a first side opposite a second side, and comprising an electrolyte disposed on the first side, the second side, or a combination thereof,
a plurality of first electrodes disposed on the substrates in ionic communication with the electrolyte;
a plurality of second electrodes disposed on the substrates in ionic communication with the electrolyte and electrically isolated from the plurality of first electrodes;
wherein the plurality of substrates and the plurality of spacer elements define a plurality of first passages in fluid communication with the first electrodes and a plurality of second passages in fluid communication with the second electrodes.

Embodiment 17

The solid oxide cell of any one of embodiments 11-16, wherein the substantially-planar substrates comprise glass.

Embodiment 18

The solid oxide cell of any one of embodiments 11-17, wherein the plurality of spacer elements comprise glass.

Embodiment 19

The solid oxide cell of any one of embodiments 11-18, wherein the plurality of spacer elements comprises glass capillary tubes.

Embodiment 20

The solid oxide cell of any one of embodiments 11-19, wherein the electrolyte comprises
a first interface between an yttria-stabilized zirconia material and the substrate, and
a second interface between a platinum oxide material and the yttria-stabilized zirconia material.

Embodiment 21

The solid oxide cell of any one of embodiments 11-20, wherein the first interface, the second interface, or both, are adapted to provide ionic communication between at least one of the first electrodes and at least one of the second electrodes.

Embodiment 22

The solid oxide cell of any one of embodiments 11-21, further comprising one or more interfacial catalysts disposed where the electrolyte is in ionic communication with one or more of the first electrodes, one or more of the second electrodes, or a combination thereof.

Embodiment 23

The solid oxide cell of any one of embodiments 11-22, wherein the one or more interfacial catalysts are chosen from Li, Ti, Cr, Mn, Fe, Co, Ni, Sr, Sn, Ce, Sm, Gd, Na, K, Cl, and combinations of two or more thereof.

Embodiment 24

The solid oxide cell of any one of embodiments 11-23, wherein the one or more interfacial catalysts are present in the form of metal oxides, metal nanopowders, or a combination thereof.

Embodiment 25

The solid oxide cell of any one of embodiments 11-24, wherein the plurality of first passages are adaptable to provide an oxygen-containing gas to the plurality of first electrodes.

Embodiment 26

The solid oxide cell of any one of embodiments 11-25, wherein the plurality of second passages are adaptable to provide a fuel-containing gas to the plurality of second electrodes.

Embodiment 27

The solid oxide cell of any one of embodiments 11-26, wherein the fuel-containing gas comprises hydrogen.

Embodiment 28

The solid oxide cell of any one of embodiments 11-27, further comprising an oxygen-containing gas input manifold sealably connected to the plurality of first passages.

Embodiment 29

The solid oxide cell of any one of embodiments 11-28, wherein the oxygen-containing gas input manifold comprises a device for applying an ion-conducting species to the plurality of first electrodes.

Embodiment 30

The solid oxide cell of any one of embodiments 11-29, wherein the device is adapted to provide a mist or aerosol of the ion-conducting species to the plurality of first electrodes.

Embodiment 31

The solid oxide cell of any one of embodiments 11-30, wherein the device is adapted to provide a bolus of ion-conducting species to the plurality of first passages.

Embodiment 32

The solid oxide cell of any one of embodiments 11-31, further comprising an oxygen-containing gas exhaust manifold sealably connected to the plurality of first passages.

Embodiment 33

The solid oxide cell of any one of embodiments 11-32, further comprising a fuel gas input manifold sealably connected to the plurality of second passages.

Embodiment 34

The solid oxide cell of any one of embodiments 11-33, further comprising a fuel gas exhaust manifold sealably connected to the plurality of second passages.

Embodiment 35

The solid oxide cell of any one of embodiments 11-34, wherein the plurality of first electrodes and the plurality of second electrodes are adapted to connect in electrical communication to an external circuit.

Embodiment 36

The solid oxide cell of any one of embodiments 11-35, further comprising a rig for mechanically supporting the plurality of substrates.

Embodiment 37

The solid oxide cell of any one of embodiments 11-36, wherein the rig further comprises at least one device for compressing the substantially-planar substrates in a direction normal to the plane of the substrates.

Embodiment 38

The solid oxide cell of any one of embodiments 11-37, wherein the at least one device for compressing comprises a plate to contact a substrate and a turn screw to compress the substrates relative to the rig.

Embodiment 39

A method of making a solid oxide cell, comprising:
applying a first metal compound to a substrate, and
exposing the first metal compound to an environment that will convert at least some of the first metal compound to a first metal oxide, thereby forming a substrate having electrolyte;
at least partially assembling the cell to comprise a plurality of the substrates having electrolyte, wherein the plurality of substrates are separated by a plurality of spacer elements;
applying an electrode composition to the substrates, wherein the electrode composition comprises a conductive particle and a second metal compound that is alike or different than the first metal compound, and
exposing the second metal compound to an environment that will convert at least some of the second metal compound to a second metal oxide that is alike or different than the first metal oxide, thereby forming electrodes on the substrates, wherein the electrodes are in ionic communication with the electrolyte;
thereby forming the solid oxide cell.

Embodiment 40

The method of embodiment 39, wherein the substrate comprises glass.

Embodiment 41

The method of any one of embodiments 39-40, wherein the first metal compound comprises a zirconium metal compound.

Embodiment 42

The method of any one of embodiments 39-41, comprising further applying an yttrium metal compound with the first metal compound.

Embodiment 43

The method of any one of embodiments 39-42, wherein the exposing comprises heating.

Embodiment 44

The method of any one of embodiments 39-43, wherein the spacer elements comprise glass.

Embodiment 45

The method of any one of embodiments 39-44, wherein the spacer elements comprise glass capillary tubes.

Embodiment 46

The method of any one of embodiments 39-45, wherein the conductive particle comprises silver-coated nickel flakes, silver-coated nickel spheres, silver nanoparticles, or a combination of two or more thereof.

Embodiment 47

The method of any one of embodiments 39-46, wherein the electrode composition comprises a zirconium metal compound.

Embodiment 48

The method of any one of embodiments 39-47, wherein the electrode composition comprises an yttrium metal compound.

Embodiment 49

The method of any one of embodiments 39-48, wherein the electrode composition comprises a platinum metal compound.

Embodiment 50

The method of any one of embodiments 39-49, wherein the applying an electrode composition to the substrates is performed under reduced pressure.

Embodiment 51

The method of any one of embodiments 39-50, wherein the electrolyte on the substrate forms an interface adapted to allow ionic conductivity along the interface.

Embodiment 52

The method of any one of embodiments 39-51, wherein the applying a first metal compound comprises dip coating or spin coating.

Embodiment 53

The method of any one of embodiments 39-52, wherein the applying a first metal compound comprises dip coating.

Embodiment 54

The method of any one of embodiments 39-53, further comprising adding an ion-conducting species to at least some of the electrodes.

Embodiment 55

The method of any one of embodiments 39-54, wherein the ion-conducting species is hydrophobic or hydrophilic.

Embodiment 56

The method of any one of embodiments 39-55, wherein the ion-conducting species is hydrophilic.

Embodiment 57

The method of any one of embodiments 39-54, wherein the ion-conducting species is chosen from water, salt water, an ionic liquid, and inorganic salt, and combinations thereof.

Embodiment 58

The method of any one of embodiments 39-57, wherein the ion-conducting species comprises tetrafluoroborate, potassium permanganate, NaCl, KCl, or a combination of two or more thereof.

Embodiment 59

The method of any one of embodiments 39-58, further comprising:
before applying an electrode composition,
applying a platinum metal compound to the electrolyte, and exposing the platinum metal compound to an environment that will convert at least some of the platinum metal compound to a platinum oxide.

Embodiment 60

A method of operating a solid oxide cell that comprises a first electrode and a second electrode, electrically isolated from each other and in ionic communication with an electrolyte, the method comprising:
contacting at least one of the electrodes with an ion-conducting species.

Embodiment 61

The method of embodiment 60, wherein the ion-conducting species is chosen from water, salt water, an ionic liquid, an inorganic salt, and combinations of two or more thereof.

Embodiment 62

The method of any one of embodiments 60-61, wherein the ion-conducting species comprises tetrafluoroborate, potassium permanganate, NaCl, KCl, or a combination of two or more thereof.

Embodiment 63

The method of operating a solid oxide cell of embodiments 61-62,
which cell comprises an electrolyte comprising at least one interface between an yttria-stabilized zirconia material and a glass material, a first electrode and a second electrode electrically isolated from each other and in ionic communication with the electrolyte, the method comprising:
connecting the first electrode in electrical communication to an external circuit;

connecting the second electrode in electrical communication to the external circuit;
providing an oxygen-containing gas to the first electrode;
providing a fuel-containing gas to the second electrode; and
heating or maintaining the cell to a temperature at which the cell provides electrical energy to the external circuit.

Embodiment 64

The method of any one of embodiments 61-63, wherein the temperature is no greater than 250° C.

Embodiment 65

The method of any one of embodiments 61-63, wherein the temperature is no greater than 200° C.

Embodiment 66

The method of any one of embodiments 61-63, wherein the temperature is no greater than 150° C.

Embodiment 67

The method of any one of embodiments 61-63, wherein the temperature is no greater than 100° C.

Embodiment 68

The method of any one of embodiments 61-63, wherein the temperature is no greater than 50° C.

Embodiment 69

The method of any one of embodiments 61-63, wherein the temperature is no greater than 30° C.

Embodiment 70

The method of any one of embodiments 61-69, further comprising cooling the cell.

Embodiment 71

The method of any one of embodiments 61-70, further comprising contacting the first electrode with an ion-conducting species.

Embodiment 72

The method of any one of embodiments 61-71, wherein the electrolyte further comprises a platinum oxide material proximal to the yttria-stabilized zirconia material.

Embodiment 73

The method of any one of embodiments 61-72, wherein the electrolyte further comprises a platinum oxide material in ionic communication with the first electrode, the second electrode, or both.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

We claim:

1. A method of operating a solid oxide fuel cell that comprises an oxygen electrode and a fuel electrode, electrically isolated from each other and in ionic communication with an electrolyte, the method comprising:
   providing an oxygen-containing gas to the oxygen electrode;
   providing a fuel-containing gas to the fuel electrode, wherein the fuel-containing gas is hydrogen;
   contacting the oxygen electrode with a liquid ion-conducting species, wherein the liquid ion-conducting species is water; and
   heating or maintaining the solid oxide fuel cell to a temperature at which the solid oxide fuel cell provides electrical energy to an external circuit, wherein the temperature is no greater than 200° C.

2. A method of operating a solid oxide cell, which cell comprises an electrolyte comprising at least one interface between an yttria-stabilized zirconia material and a glass material, a first electrode and a second electrode electrically isolated from each other and in ionic communication with the electrolyte, the method comprising:
   connecting the first electrode in electrical communication to an external circuit;
   connecting the second electrode in electrical communication to the external circuit;
   providing an oxygen-containing gas to the first electrode;
   providing a fuel-containing gas to the second electrode, wherein the fuel-containing gas is hydrogen;
   contacting the first electrode with a liquid ion-conducting species; and
   heating or maintaining the cell to a temperature at which the cell provides electrical energy to the external circuit.

3. The method of claim 2, wherein the temperature is no greater than 250° C.

4. The method of claim 2, wherein the temperature is no greater than 200° C.

5. The method of claim 2, wherein the temperature is no greater than 150° C.

6. The method of claim 2, wherein the temperature is no greater than 100° C.

7. The method of claim 2, wherein the temperature is no greater than 50° C.

8. The method of claim 2, wherein the temperature is no greater than 30° C.

9. The method of claim 2, further comprising cooling the cell.

10. The method of claim 2, wherein the electrolyte further comprises a platinum oxide material proximal to the yttria-stabilized zirconia material.

11. The method of claim 2, wherein the electrolyte further comprises a platinum oxide material in ionic communication with the first electrode, the second electrode, or both.

12. The method of claim 1, wherein the temperature is no greater than 150° C.

13. The method of claim 1, wherein the temperature is no greater than 100° C.

14. The method of claim 1, wherein the temperature is no greater than 50° C.

15. The method of claim 1, wherein the temperature is no greater than 30° C.

* * * * *